(12) United States Patent
Stanfield et al.

(10) Patent No.: US 12,383,721 B2
(45) Date of Patent: Aug. 12, 2025

(54) VENTRICULAR ASSIST SYSTEM AND METHOD OF TREATMENT OF CARDIOVASCULAR IMPAIRMENT

(71) Applicant: STAR BP, INC., Spring, TX (US)

(72) Inventors: J. Ryan Stanfield, Sandy, UT (US); Landon Tompkins, Peachtree Corners, GA (US); Michael Vladovich, Edmond, OK (US); Matthew Keillor, Sain Sebastien sur Loire (FR)

(73) Assignee: STAR BP, INC., Spring, TX (US)

( * ) Notice: Subject to any disclaimer, the term of this patent is extended or adjusted under 35 U.S.C. 154(b) by 0 days.

(21) Appl. No.: 18/836,090

(22) PCT Filed: Nov. 20, 2023

(86) PCT No.: PCT/US2023/080502
§ 371 (c)(1),
(2) Date: Aug. 6, 2024

(87) PCT Pub. No.: WO2024/112648
PCT Pub. Date: May 30, 2024

(65) Prior Publication Data
US 2025/0108199 A1 Apr. 3, 2025

Related U.S. Application Data

(60) Provisional application No. 63/426,957, filed on Nov. 21, 2022.

(51) Int. Cl.
*A61M 60/122* (2021.01)
*A61M 60/90* (2021.01)

(52) U.S. Cl.
CPC .......... *A61M 60/122* (2021.01); *A61M 60/90* (2021.01); *A61M 2205/04* (2013.01)

(58) Field of Classification Search
None
See application file for complete search history.

(56) References Cited

U.S. PATENT DOCUMENTS

| 6,544,216 B1 | 4/2003 | Sammler et al. |
| 2009/0112312 A1 | 4/2009 | Larose et al. |
| 2009/0221992 A1 | 9/2009 | Hannon et al. |

(Continued)

FOREIGN PATENT DOCUMENTS

| WO | 2021156255 A1 | 8/2021 | |
| WO | WO-2022219192 A1 * | 10/2022 | .......... A61M 60/174 |

OTHER PUBLICATIONS

International Search Report and Written Opinion issued in PCT App. No. PCT/US2023/080502, dated Jun. 3, 2024 (11 pages).

*Primary Examiner* — Amanda K Hulbert
*Assistant Examiner* — Philip C Edwards
(74) *Attorney, Agent, or Firm* — Ewing & Jones, PLLC

(57) ABSTRACT

A ventricular assist system including a cannula that defines a lumen and includes a first end and a second end. The second end of the cannula includes a tip that defines an opening, and a pump operably is coupled to the first end of the cannula. A pump anchor is operably coupled to the pump. The pump anchor has a retracted position and a deployed position. A tip anchor is operably coupled to the second end of the cannula proximate the tip. A sheath is selectively disposed around the cannula, and a guidewire disposed within the lumen of the cannula.

7 Claims, 46 Drawing Sheets

(56) References Cited

U.S. PATENT DOCUMENTS

2016/0045652 A1* 2/2016 Cornen .............. A61M 60/148
                                                    600/16
2017/0340789 A1   11/2017 Bonde et al.
2019/0105437 A1*  4/2019 Siess ................. A61M 60/216
2020/0155743 A1   5/2020 Siess et al.

* cited by examiner

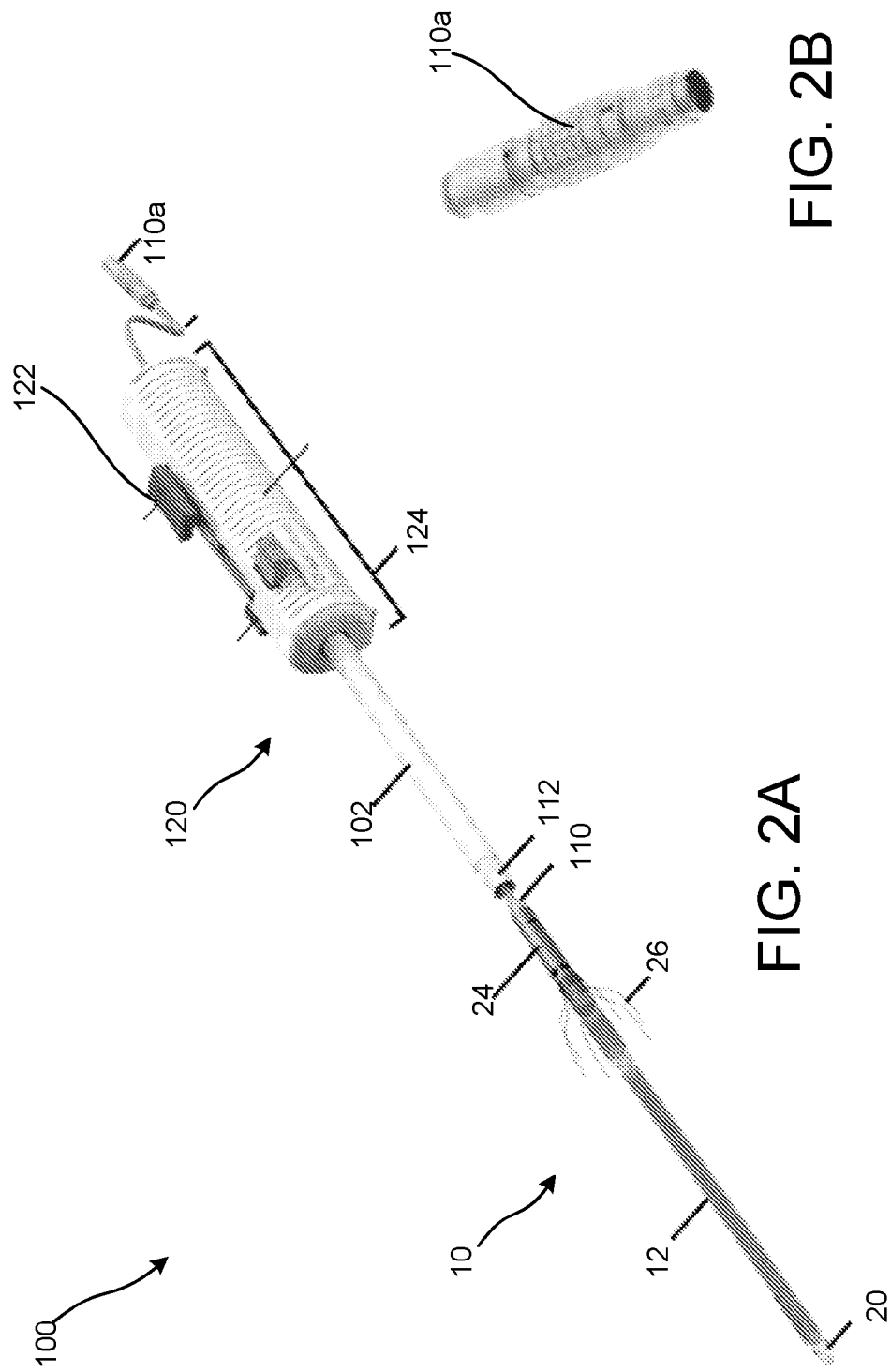

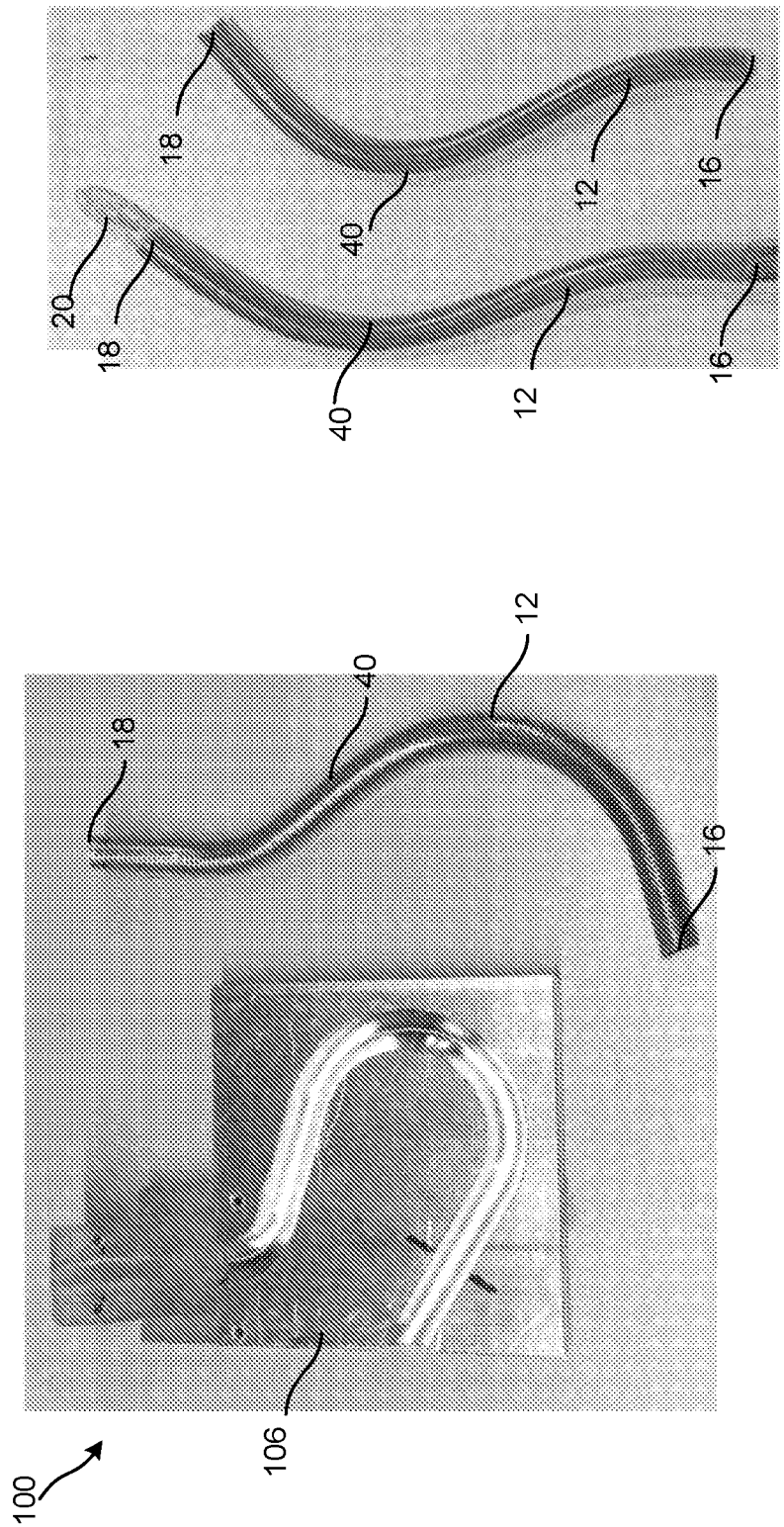

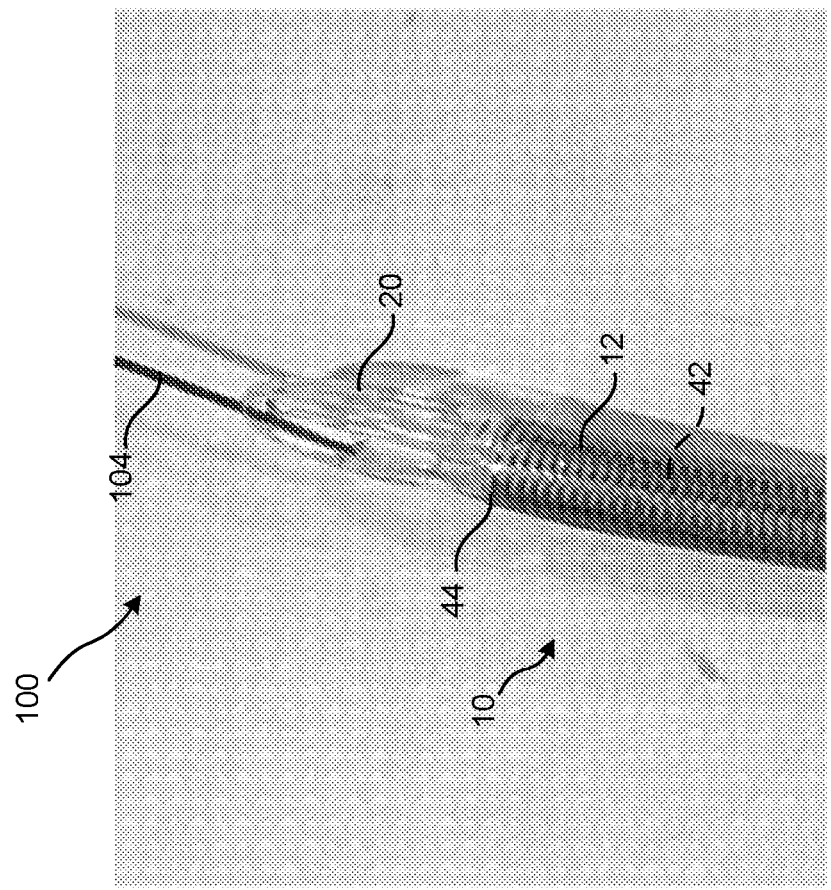
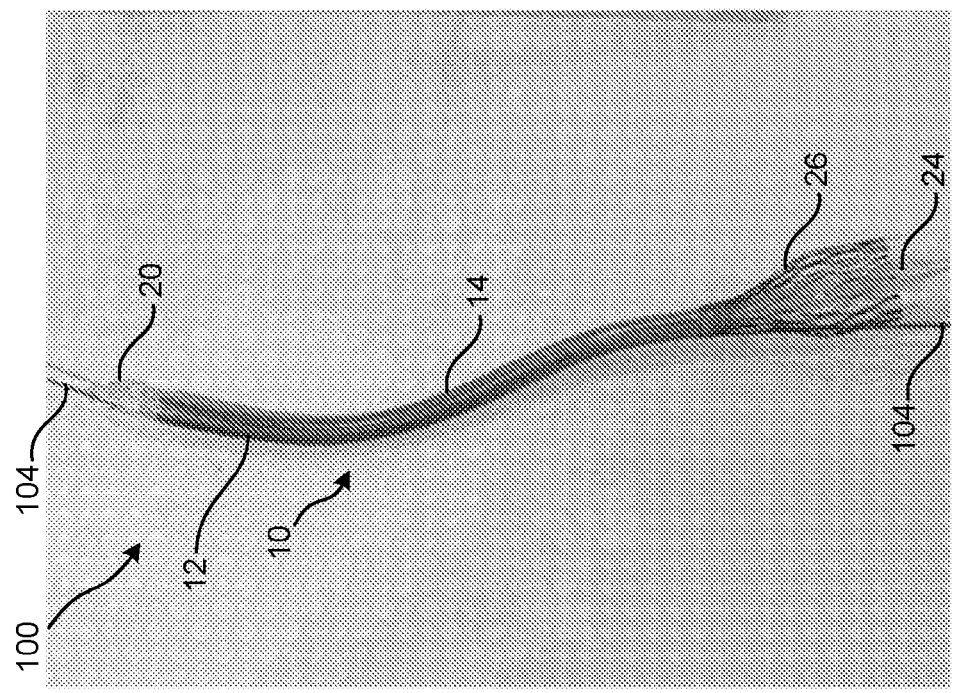
FIG. 7A
FIG. 7B

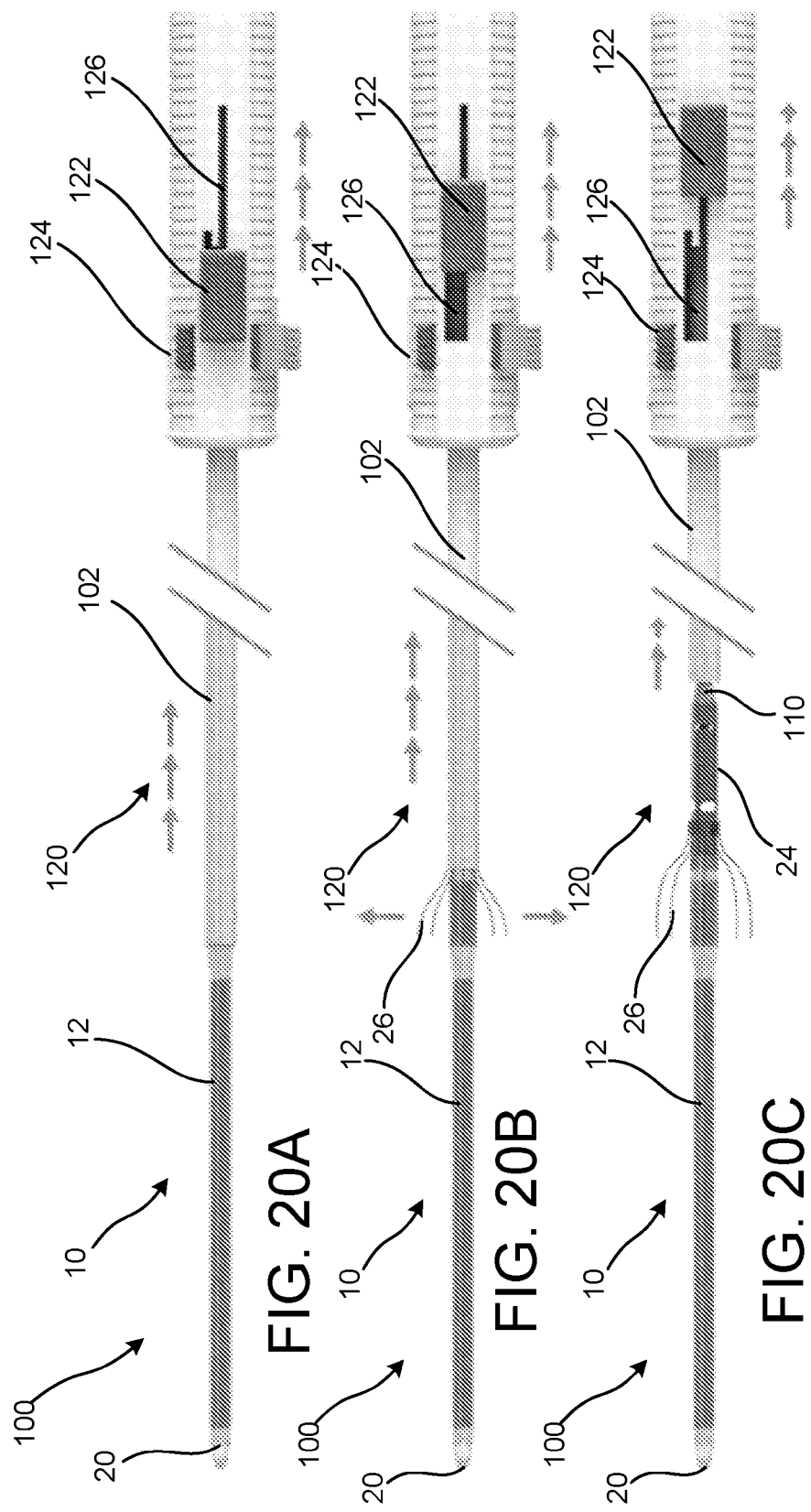

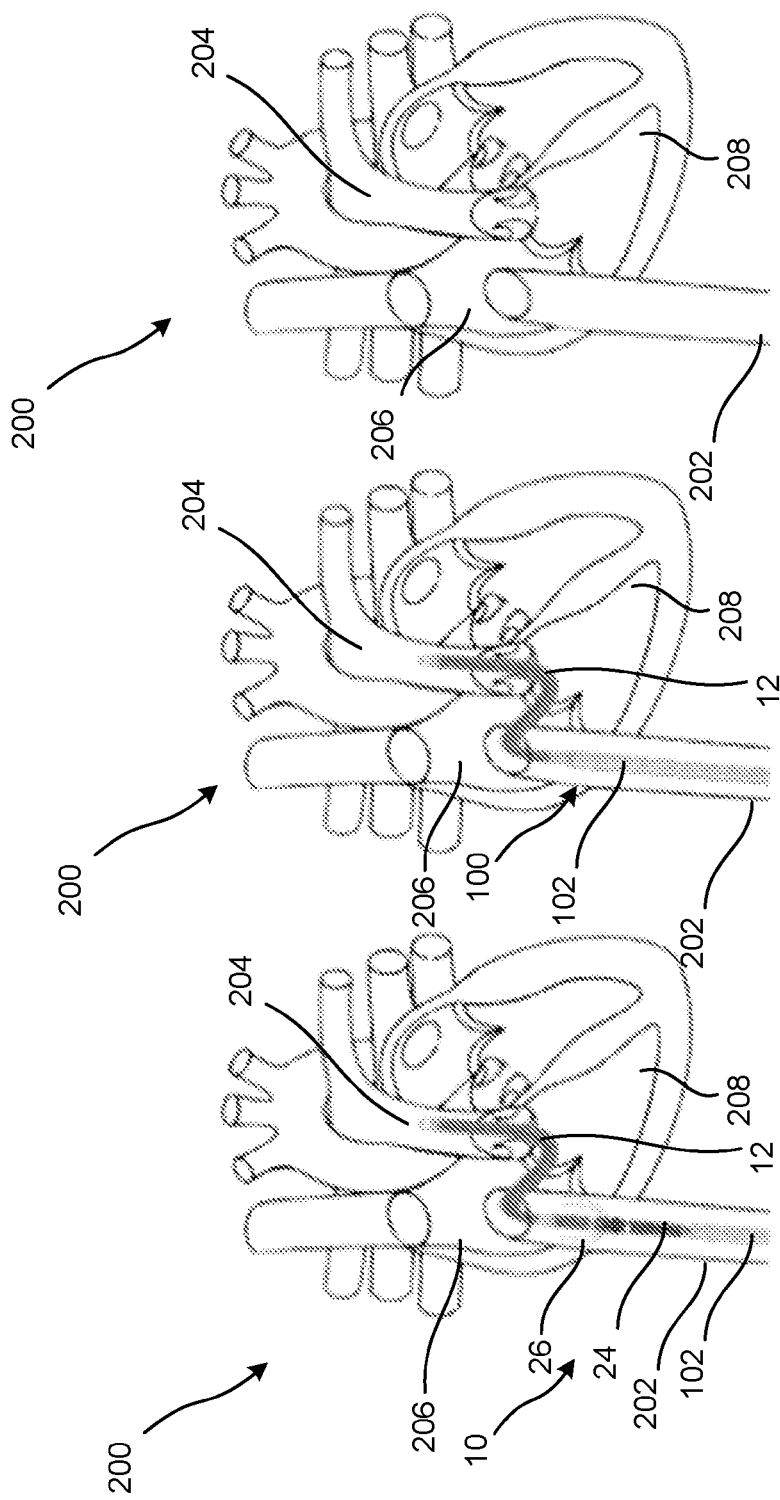

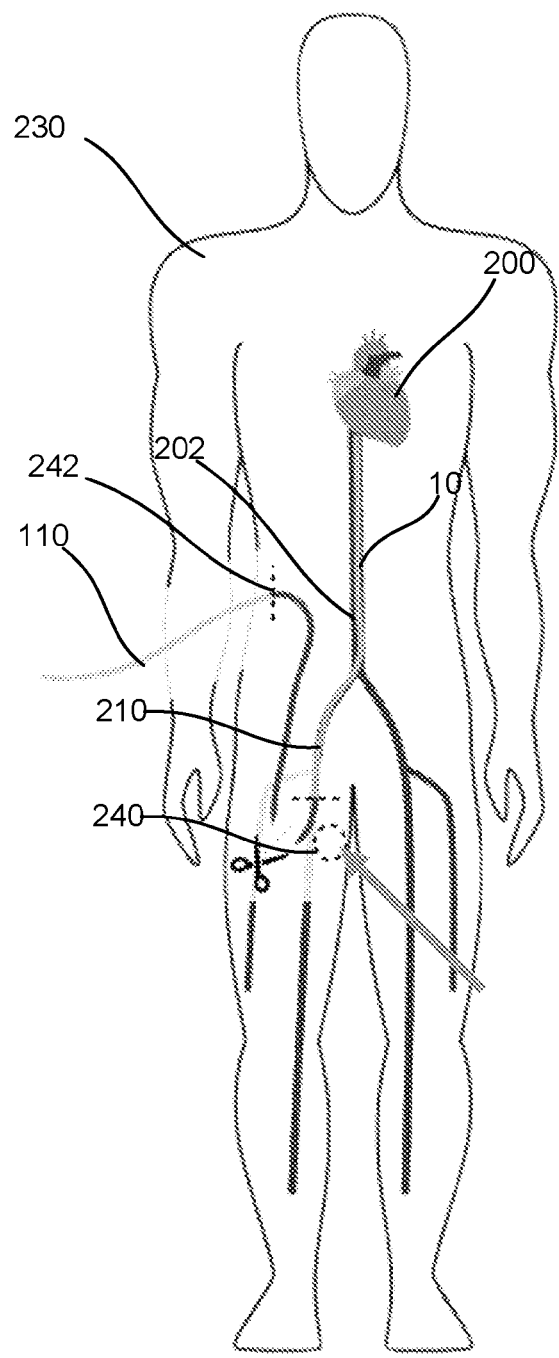
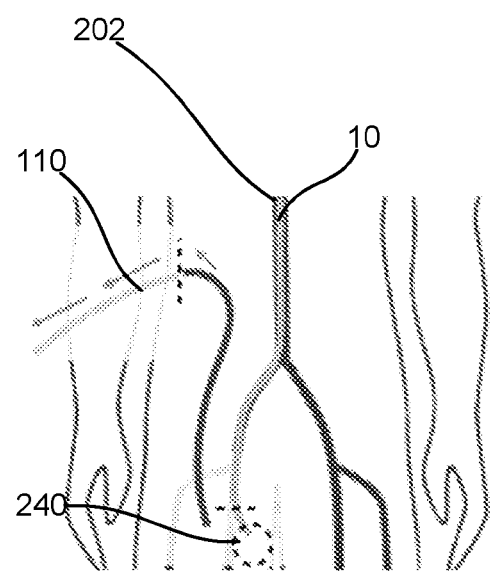
FIG. 24C
FIG. 24D

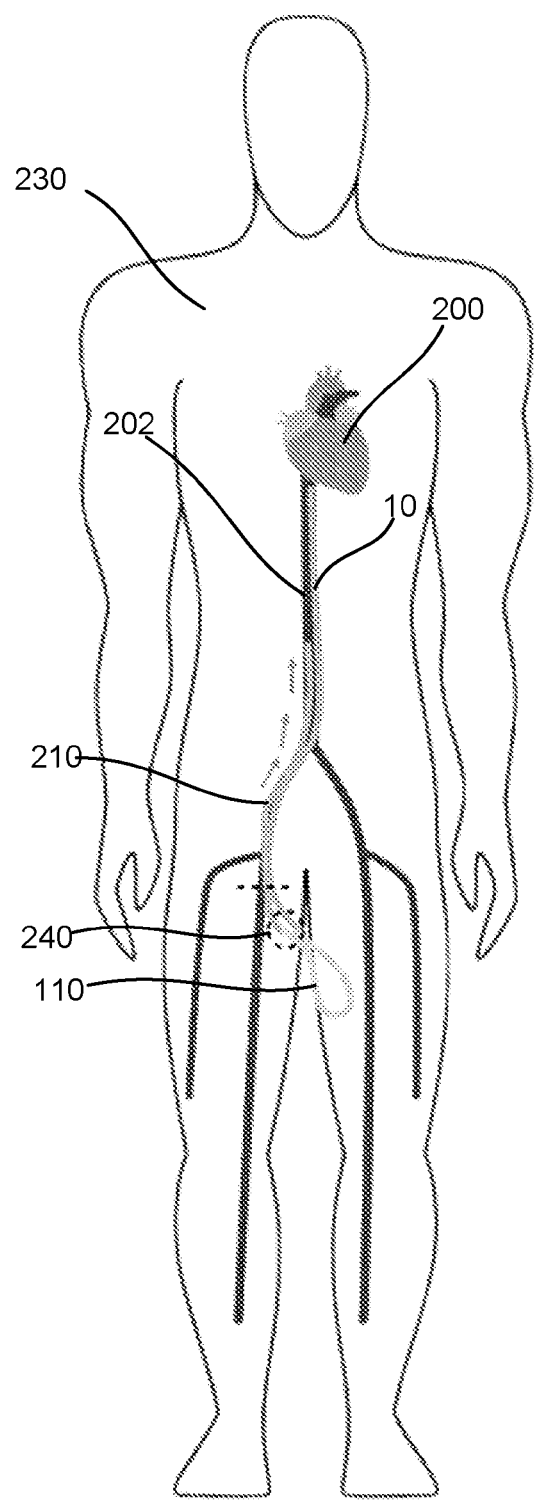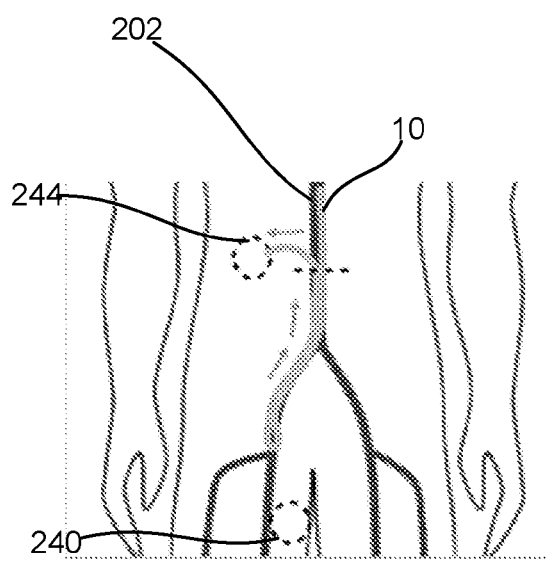
FIG. 25A
FIG. 25B

VENTRICULAR ASSIST SYSTEM AND METHOD OF TREATMENT OF CARDIOVASCULAR IMPAIRMENT

PRIORITY CLAIM

This application claims the benefit of PCT/US2023/080502 filed Nov. 20, 2023, which claims priority to U.S. Provisional Patent Application 63/426,957, filed Nov. 21, 2022, both of which are incorporated by reference herein in its entirety.

TECHNICAL FIELD

This disclosure relates to a ventricular assist system and a method of treatment using the ventricular assist system.

SUMMARY

One aspect of the disclosure provides a ventricular assist device that includes a cannula. The cannula defines a lumen and includes a first end and a second end. The second end of the cannula includes a tip that defines an opening. A pump is operably coupled to the first end of the cannula, and a pump anchor is operably coupled to the pump. The pump anchor has a retracted position and a deployed position. A tip anchor is operably coupled to the second end of the cannula proximate to the tip.

Implementations of the disclosure may include one or more of the following optional features. In some implementations, the cannula may include a semi-rigid sigmoidal body that may be defined between the first end and the second end. Optionally, the tip may have a lower arcuate portion and an upper narrow portion that may collectively define the opening. In another example, the pump anchor and the tip anchor may each include an attachment portion and a plurality of extensions that extend from the attachment portion. In this example, the pump anchor and the tip anchor may be coupled to the pump and the second end of the cannula, respectively, at the respective attachment portions. Optionally, the plurality of extensions of the pump anchor may define an interconnected net disposed around the pump.

In another implementation, the pump anchor may include a first pump anchor coupled to the pump and a second pump anchor coupled to the pump. In this implementation, each of the first and second pump anchors may include a plurality of extensions. Optionally, the plurality of extensions of the first pump anchor may extend toward the cannula, and the plurality of extensions of the second pump anchor may extend away from the cannula. According to another aspect of the disclosure, the tip anchor may have an inflatable body that has an expanded position and a contracted position. Optionally, the inflatable body defines a plurality of recesses, and at least one of the plurality of recesses may be aligned with the opening defined by the tip of the cannula. In another example, the pump anchor may have a spiral configuration.

Another aspect of the disclosure provides a ventricular assist system that includes a cannula defining a lumen. The cannula includes a first end and a second end. The system includes a pump that is operably coupled to the first end of the cannula. A pump anchor is operably coupled to the pump, and the pump anchor has a retracted position and a deployed position. The system also includes a tip anchor that is operably coupled to the second end of the cannula proximate to the tip. A sheath is selectively disposed around the cannula, and a guidewire is disposed within the lumen of the cannula.

This aspect may include one or more of the following optional features. In one example, the pump anchor may include a plurality of eyelets and a wire. In another aspect, the guidewire may include a cap removably coupled to the pump, and the guidewire may be aligned with the lumen of the cannula via the cap that may be coupled to the pump. Optionally, the sheath may define a linear body between the first end and the second end of the cannula when the sheath is disposed around the cannula. Optionally, the cannula has a sigmoidal body between the first end and the second end of the cannula when the sheath is removed from the cannula.

Another aspect of the disclosure provides a method of treatment of a cardiovascular impairment using a ventricular assist device across a right ventricular between an inferior vena cava and a pulmonary artery of a human. The method includes inserting the ventricular assist device in the interior vena cava via a delivery device and a driveline at an access site. The ventricular assist device includes a pump including at least one anchor and a cannula operably coupled to the pump. The method also includes guiding the cannula inserted into the inferior vena cava through a right atrium of the human, into the right ventricle, and into the pulmonary artery. The at least one anchor of the ventricular assist device is then deployed in the inferior vena cava, and the delivery device is removed over the driveline. When the treatment is complete, the driveline is at least partially removed from the human. The method then includes inserting the delivery device over the driveline and into the inferior vena cava. The method also includes collapsing the at least one anchor of the ventricular assist device and removing the delivery device and the ventricular assist device from said human.

This aspect may include one or more of the following optional steps and features. Optionally, the method may include inserting the driveline subcutaneously proximate to the access site and guiding, subcutaneously, the driveline toward a lower abdomen. In this example, the end of the driveline may be removed at an exit site that may be located at the lower abdomen. In another aspect, the access site may be proximate to a femoral vein. In an alternate aspect, the access site may be proximate to the inferior vena cava. In another implementation, the method may include partially removing the driveline at the access site, where the access site is proximate to a femoral vein, and bending the driveline extracorporeally. This example method may also include reinserting the driveline into a lower portion of the inferior vena cava from the access site, guiding an end of the driveline, subcutaneously, toward a lower abdomen from an exit site defined at the lower portion of the inferior vena cava, and removing the end of the driveline at a treatment site located at the lower abdomen. In another aspect, the method may include removing the driveline from the human by cutting the driveline.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2A is a perspective view of a ventricular assist device of the present disclosure;

FIG. 2B is a perspective view of a connector of a driveline of a ventricular assist device of the present disclosure;

FIG. 3A is a perspective view of a mold and a body of a cannula of the present disclosure;

FIG. 3B is a perspective view of a cannula of a ventricular assist device of the present disclosure;

FIG. 7A is a perspective view of a ventricular assist device of the present disclosure with a guidewire inserted in a lumen of a cannula;

FIG. 7B is an enlarged partial perspective view of a tip of the cannula of FIG. 7 with the guidewire partially inserted into the lumen;

FIGS. 20A-20C are plan views of a ventricular assist system of the present disclosure with a delivery device retracting a sheath from a ventricular assist device of the present disclosure;

FIGS. 21A-21C are schematics of a ventricular assist system of the present disclosure being removed from a heart;

FIGS. 24C-24E are schematics of the ventricular assist system of FIGS. 24A and 24B and depict removal of the ventricular assist system of the present disclosure;

FIGS. 25A and 25B are schematics of the ventricular assist system of FIGS. 23A and 23B and depict repositioning of a driveline of the present disclosure toward a treatment site from an access site;

Like reference symbols in the various drawings indicate like elements.

DETAILED DESCRIPTION

Figure 1A:
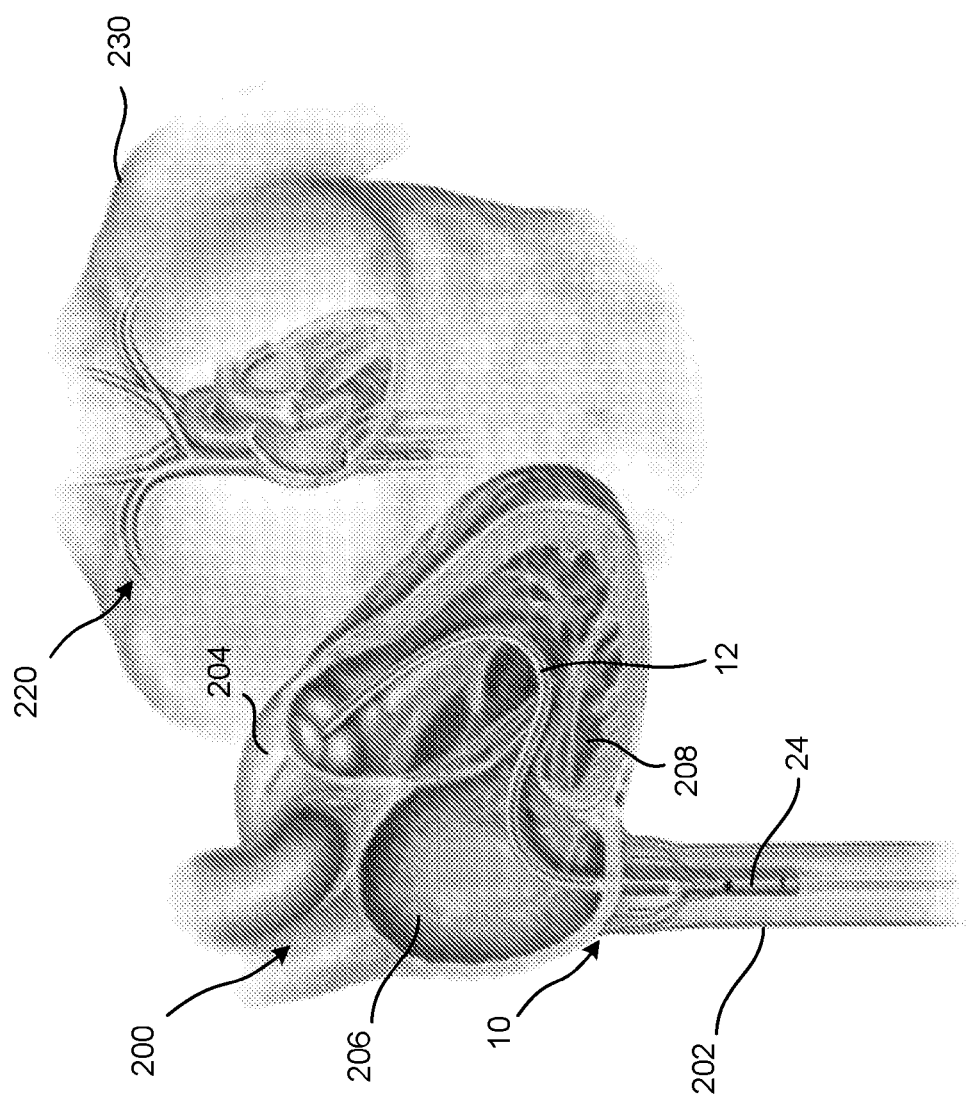
FIGS. 1A and 1B are schematics of a cross-sectional heart with a ventricular assist device of the present disclosure.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Referring to FIGS. 1A-27, reference numeral 10 generally designates a ventricular assist device for a ventricular assist system 100. The ventricular assist device 10 includes a cannula 12 that defines a lumen 14. The cannula 12 includes a first end 16 and a second end 18. The second end 18 of the cannula 12 includes a tip 20 that defines an opening 22. A pump 24 is operably coupled to the first end 16 of the cannula 12, and a pump anchor 26 is operably coupled to the pump 24. The pump anchor 26 has a retracted position and a deployed position. A tip anchor 28 may be operably coupled to the second end 18 of the cannula 12 proximate to the tip 20.

Referring now to FIGS. 1A-6B, the ventricular assist device 10 is illustrated as inserted into a heart 200 of a human. The ventricular assist device 10 is positioned inside an inferior vena cava 202 with the cannula 12 ultimately exiting the heart 200 through a pulmonary artery 204. The cannula 12 extends from a right atrium 206 and across a right ventricle 208 of the heart to enter the pulmonary artery 204. The ventricular assist system 100 is configured to insert and deploy the ventricular assist device 10 within the heart 200 to assist in a treatment of a cardiovascular impairment, as described below. The ventricular assist system 100 includes, in addition to the ventricular assist device 10, a sheath 102 and a guidewire 104. The sheath 102 is selectively disposed around the cannula 12, and the guidewire 104 is disposed within the lumen 14 of the cannula 12. As illustrated in FIG. 2, the sheath 102 may be selectively removed from the cannula 12 to deploy the pump anchor 26 within the inferior vena cava 202. The sheath 102 may be utilized to collapse and cover the pump anchor 26, such that the sheath 102 may remain over the pump anchor 26 during placement of the ventricular assist device 10. Once the ventricular assist device 10 is in place, the sheath 102 may be removed to deploy the pump anchor 26.

The cannula 12 may have a semi-rigid body 40 having a sigmoidal shape that, as illustrated in FIG. 3, is defined between the first end 16 and the second end 18. The body 40 may include an internal spiral structure 42 positioned within the lumen 14 of the cannula 12 and may provide general flexibility for the body 40 during positioning of the ventricular assist device 10 within the heart 200. For example, the lumen 14 may be formed from a polymer conduit and the spiral structure 42 may be formed from a metal structure that is positioned within the polymer conduit. The spiral structure 42 may have a range of dimension between each coil, such that the shape of the body 40 may be altered based on the coil spacing of the spiral structure 42.

Figure 4A:
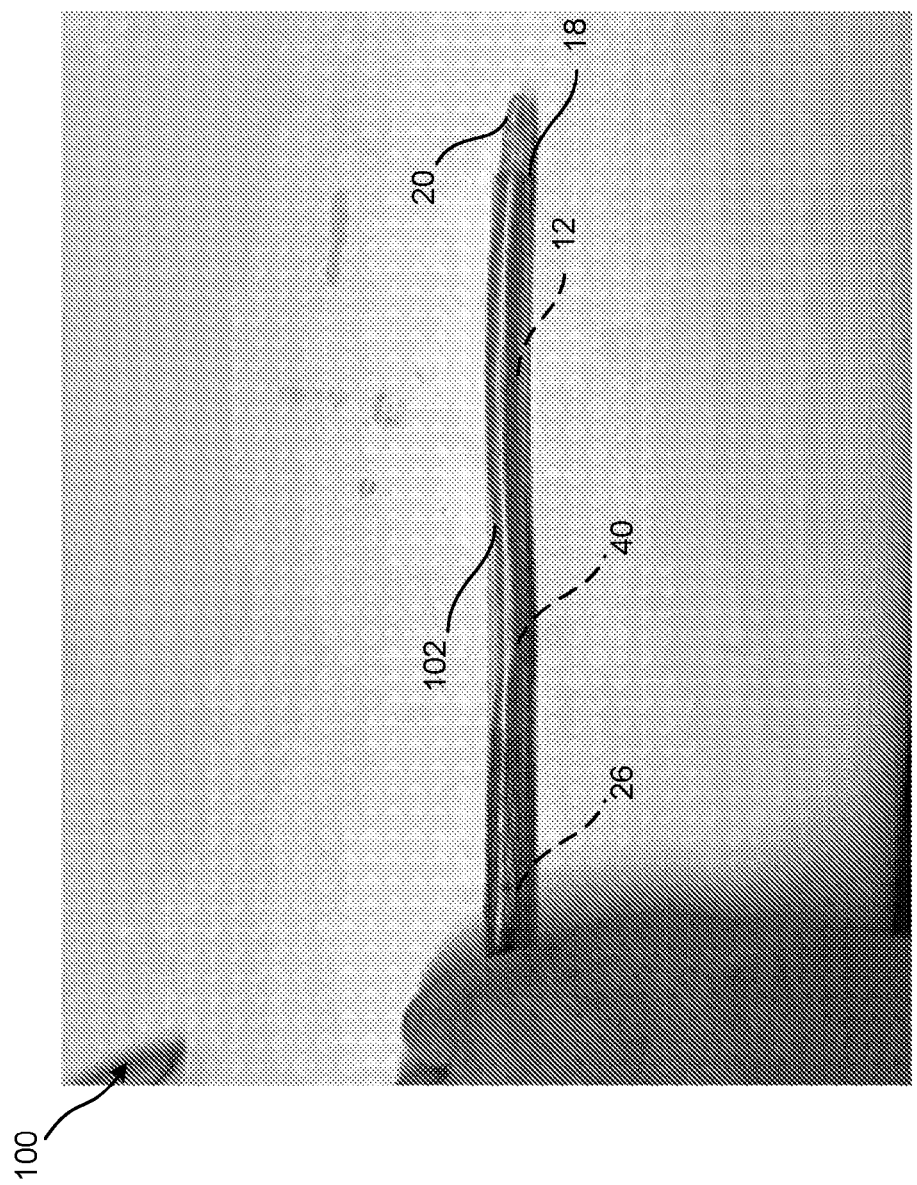
FIG. 4A is a plan view of a cannula within a sheath of the present disclosure with the cannula in a linear configuration.
Figure 4B:
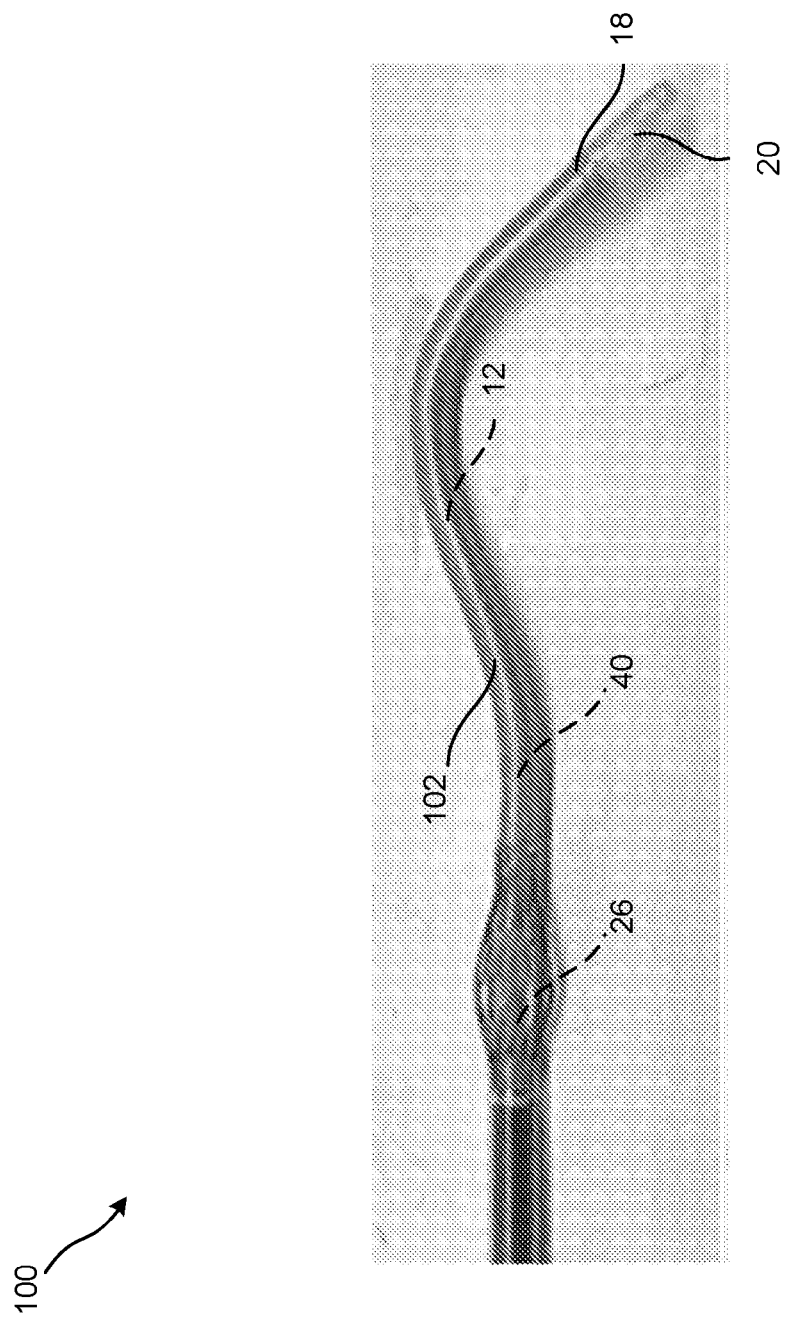
FIG. 4B is a plan view of the cannula of FIG. 4 with the sheath partially withdrawn and the cannula in a sigmoidal configuration.
Figure 5:
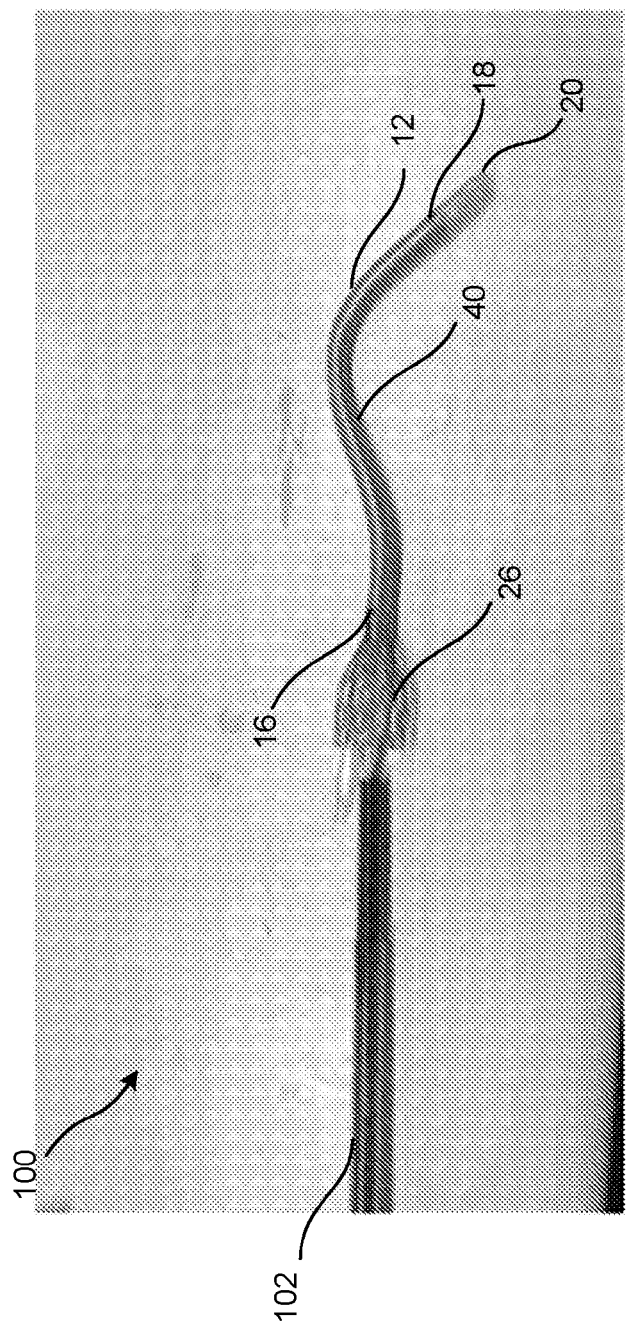
FIG. 5 is a plan view of the cannula of FIGS. 4A and 4B with the sheath withdrawn and the cannula in a sigmoidal configuration.
Figure 6B:
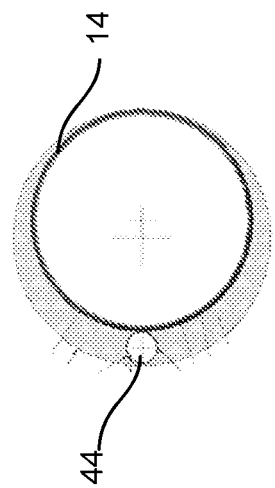
FIG. 6B is a cross-sectional view of a lumen of the cannula of FIG. 6A with a secondary lumen for receiving the guidewire.
Figure 6A:
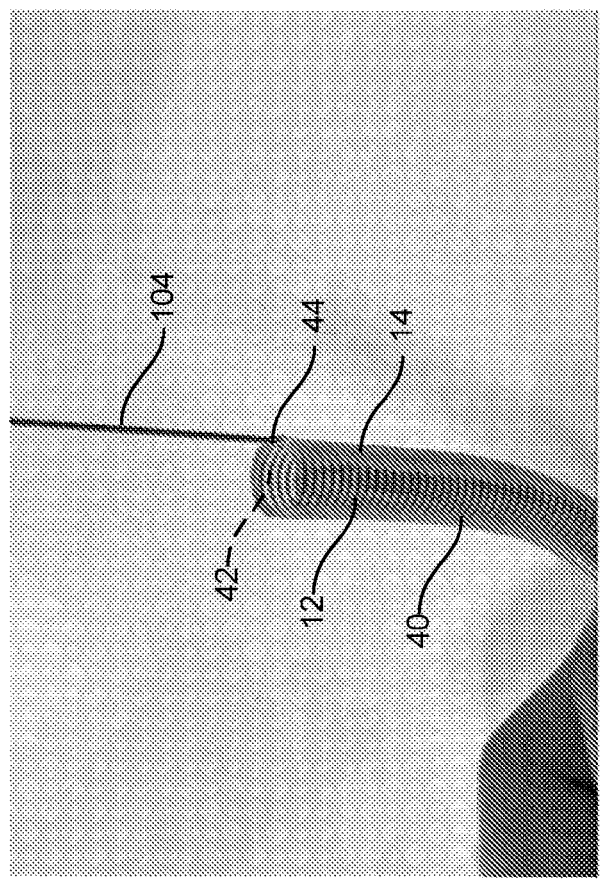
FIG. 6A is an enlarged partial perspective view of a cannula of the present disclosure with a guidewire partially inserted into a lumen of the cannula.
Figure 8:
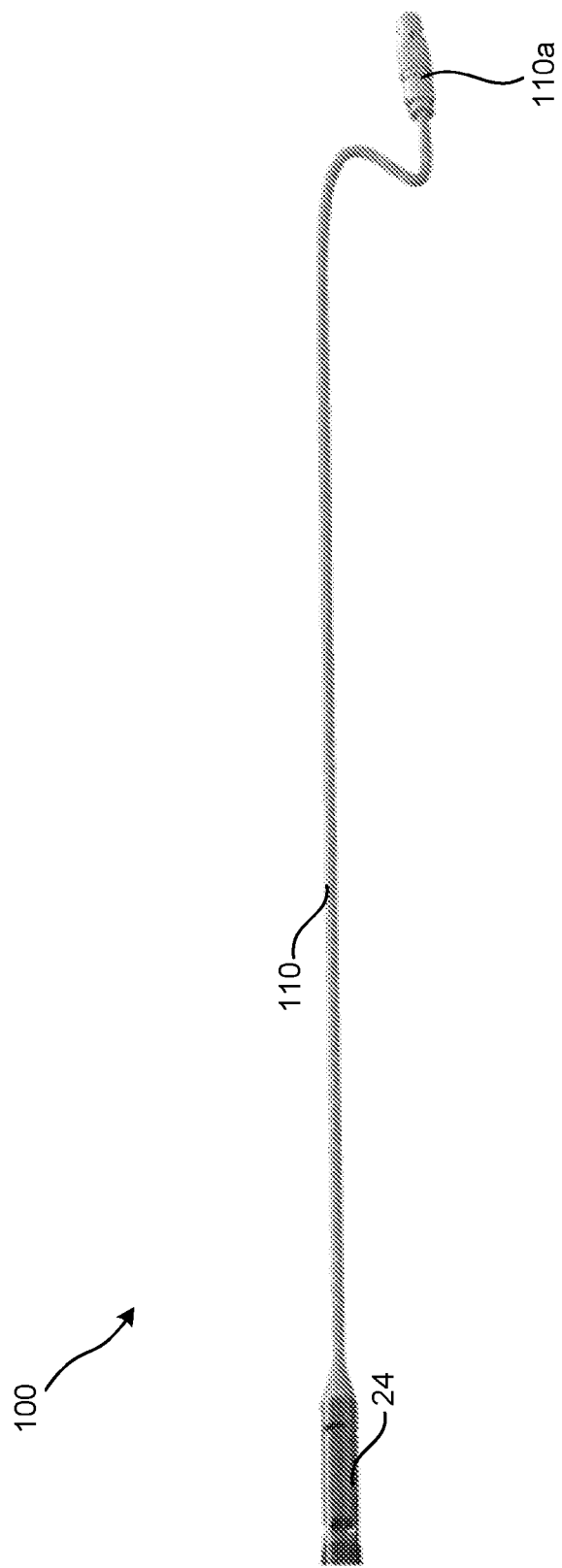
FIG. 8 is a perspective view of a driveline of the present disclosure attached to a pump and with a connector.
Figure 9:
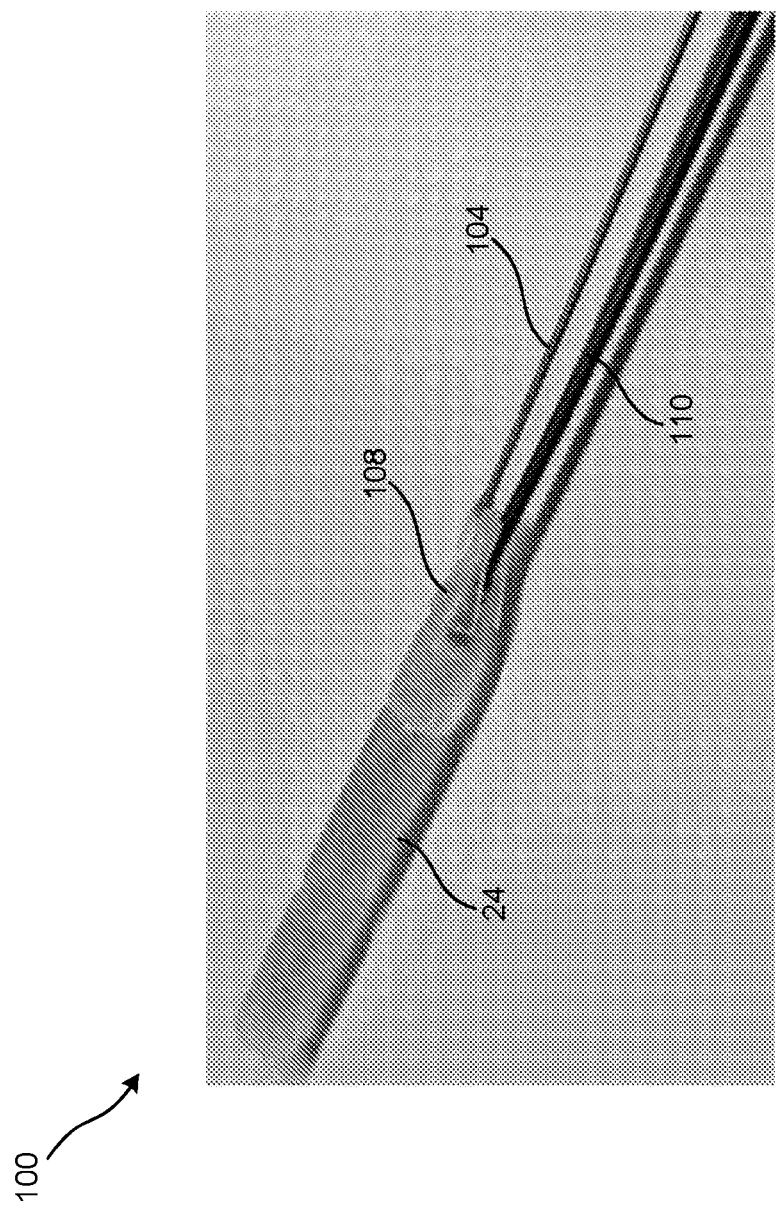
FIG. 9 is an enlarged partial perspective view of an alignment feature coupled to a ventricular assist device of the present disclosure via a cap.
Figure 10:
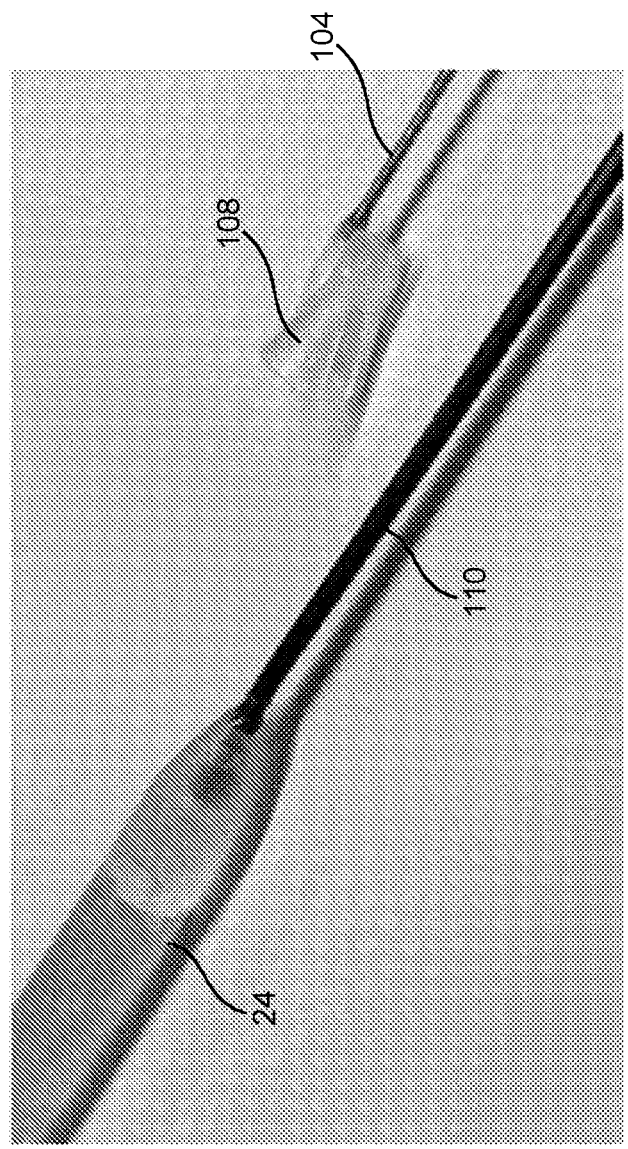
FIG. 10 is an enlarged partial perspective view of the alignment feature and cap of FIG. 9 removed from the ventricular assist device.

With further reference to FIGS. 1-6, the body 40 may be pre-shaped with the spiral structure within the lumen 14 to define the sigmoidal configuration, such that the pre-shaped nature of the body 40 retains the shape of the cannula 12, while the spiral structure 42 provides general flexibility to the otherwise semi-rigid body 40. The cannula 12 may be formed from a plurality of laminated polymer tubes with a metal coil reinforcement between layers. The polymer tubes may be formed from any practicable material including, but not limited to, polypropylene, polyvinyl chloride (PVC), thermoplastic polyurethane (TPU), and/or polytetrafluoroethylene (PFTE). The metal coil may be formed using any practicable material including, but not limited to, metal or metal alloys such as stainless steel or titanium, shape memory alloy (e.g., nickel titanium (NiTi)), or a polymer (e.g., polyether ether ketone (PEEK)). It is generally contemplated that the body 40 of the cannula 12 may be formed using a heat set process using a mold 106 to set the shape of the body 40. The shape formed by the mold 106 is configured to mimic the path from the inferior vena cava, where the cannula 12 starts, to the pulmonary artery, where the cannula 12 ends at the tip 20. As illustrated in FIGS. 4 and 5, the sheath 102 may be disposed over the body 40 to define a generally linear configuration, and when the sheath 102 is removed (FIG. 5), the body 40 returns to the pre-formed sigmoidal configuration. Stated differently, the sheath 102 defines a linear body 40 between the first end 16 and the second end 18 of the cannula 12 when the sheath 102 is disposed around the cannula 12, and the cannula 12 has a sigmoidal body 40 between the first end 16 and the second end 18 when the sheath 102 is removed from the cannula 12. The utilization of the sheath 102 to straighten the body 40 is described in more detail below with reference to FIGS. 22-26F.

With reference to FIGS. 2 and 6A-11, the guidewire 104 is operably coupled to the cannula 12 to assist in placement of the ventricular assist device 10 within the inferior vena cava 202. In one implementation illustrated in FIGS. 6A-8, the guidewire 104 is positioned within the lumen 14 proximate the spiral structure 42. The guidewire 104 may be inserted through and/or extend from the tip 20 to assist in the placement and alignment of the ventricular assist device 10 within the heart 200. For example, the lumen 14 may define a channel 44 through which the guidewire 104 may extend. The channel 44 may extend through a length L of the lumen 14, such that the guidewire 104 may extend from both the first end 16 and the second end 18 of the cannula 12. It is contemplated that the channel 44 may be formed as a secondary lumen 44 in which the guidewire 104 may be disposed. For example, the secondary lumen 44 may be formed on a radius of the lumen 14. FIG. 6B illustrates the secondary lumen 44 formed along the radius of the lumen 14 in which the guidewire 104 may be positioned. While it is contemplated that the guidewire 104 may be generally rigid and may promote a more planar configuration of the cannula 12, it is contemplated that the guidewire 104 may be sufficiently flexible so as to guide and manipulate the cannula 12 during placement of the ventricular assist device 10.

With reference now to FIGS. 8-11B, a cap 108 may be configured to have a snap-fit arrangement with the pump 24 proximate a driveline 110 of the ventricular assist system 100. The driveline 110 may be configured as a polymer extrusion and may include a plurality of wires. The driveline 110 is configured to transmit power and information between the pump 24 and an external controller of the ventricular assist system 100. The driveline 110 may also include a connector 110a (FIG. 2) at a distal end of the driveline 110 to connect the ventricular assist device 10 with the external controller. The connector 110a is an electrical connector at the distal end of the driveline 110 and is configured to interface with the external controller. In one configuration the connector 110a may have a diameter between approximately 5 millimeters and 10 millimeters. Alternatively, the driveline 110 may be free from a connector, such that the driveline 110 may be capped during implantation of the ventricular assist device 10 and separately coupled to an external connector once the driveline 110 is externalized from the body. For example, the driveline 110 may have circumferential contacts on the distal end configured to mate with the external connector. The cap 108 couples an alignment feature 112 with the pump 24, such that the alignment feature 112 and the cap 108 may be removed from the pump 24. Stated differently, the cap 108 is removably coupled to the pump 24, such that the alignment feature 112 is aligned with the lumen 14 of the cannula 12 via the cap 108 coupled to the pump 24. In this configuration, it is contemplated that the alignment feature 112 may be a stiff or generally rigid wire to assist in manipulation about the driveline 110. The cap 108 and the alignment feature 112 may be removed once the ventricular assist device 10 is positioned within the pulmonary artery 204. In a further alternate configuration, the alignment feature 112 may be configured as a tube, as illustrated in FIG. 11A. In this configuration, the alignment feature 112 extends over the driveline 110 and may be connected to the cannula 12 via the cap 108 along the driveline 110. It is contemplated that during removal, the alignment feature 112 illustrated in FIG. 11A may be separated into two pieces or otherwise pealed back. As described in more detail below, the alignment feature 112 may be removed after positioning of the ventricular assist device 10 and deployment of the pump and tip anchors 26, 28. In either configuration of the alignment feature 112, the alignment feature 112 is generally utilized to assist the alignment of the pump 24 during deployment of the ventricular assist system 100.

Figure 11A:
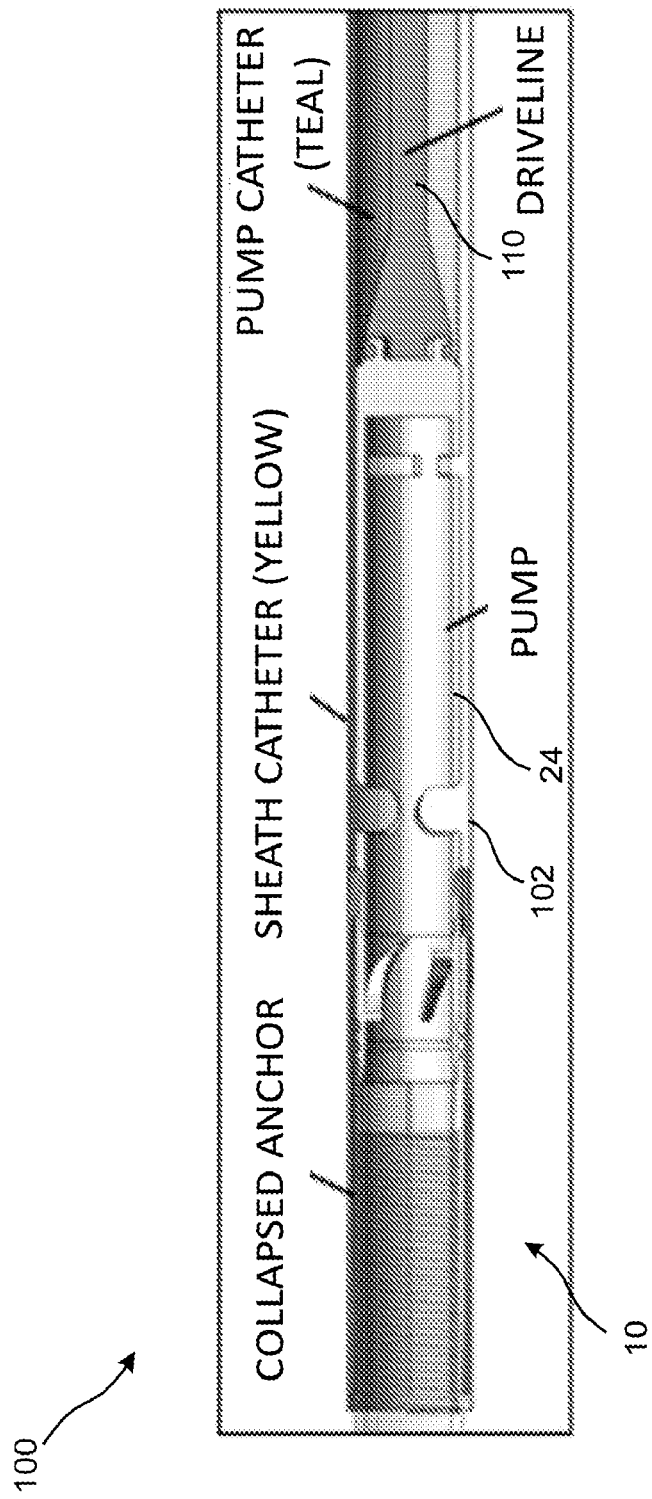
FIG. 11A is a partial side cross-sectional view of a ventricular assist device of the present disclosure with a pump and an alignment feature disposed over a driveline.
Figure 11B:
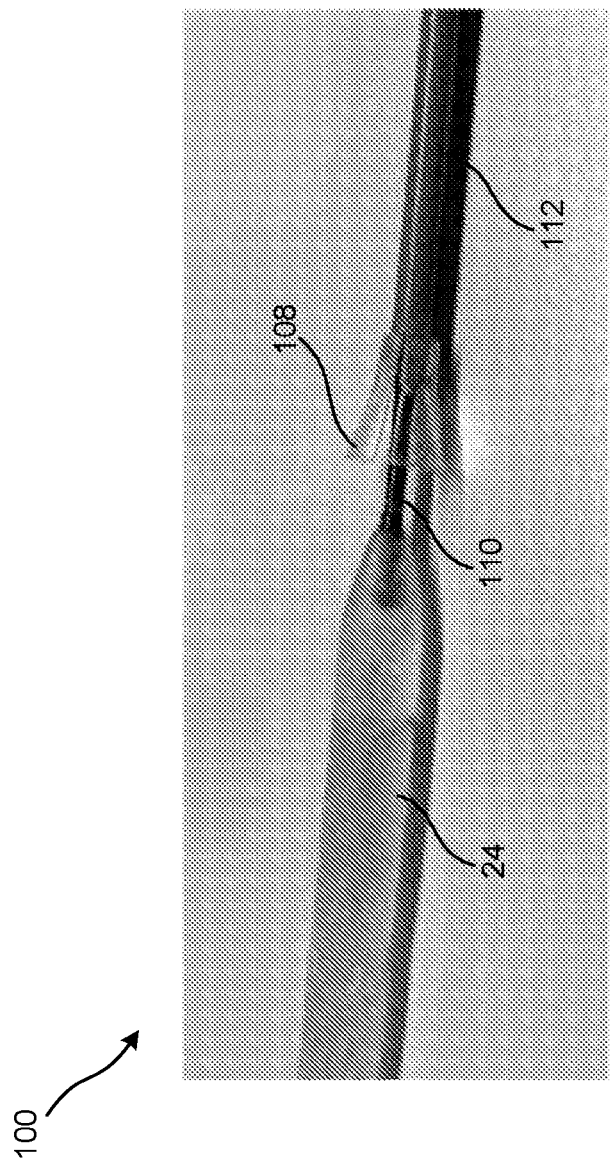
FIG. 11B is an enlarged partial perspective view of an alignment feature coupled to a driveline and proximate a ventricular assist device of the present disclosure
Figure 11D:
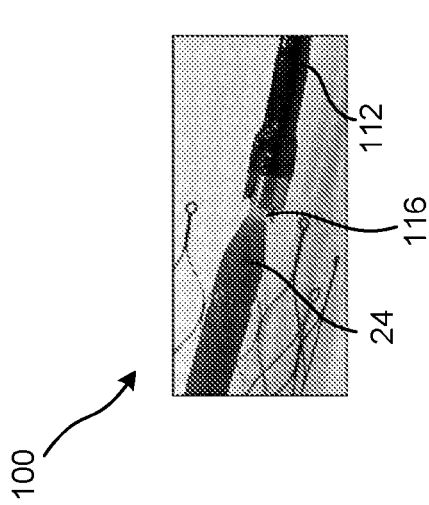
FIGS. 11C and 11D are enlarged partial perspective views of an alignment feature with a catheter tip and pins.
Figure 11E:
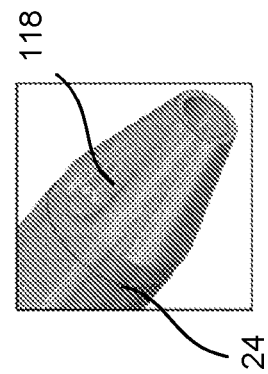
FIG. 11E is an enlarged perspective view of a pump tip of the present disclosure with indentations.
Figure 11C:
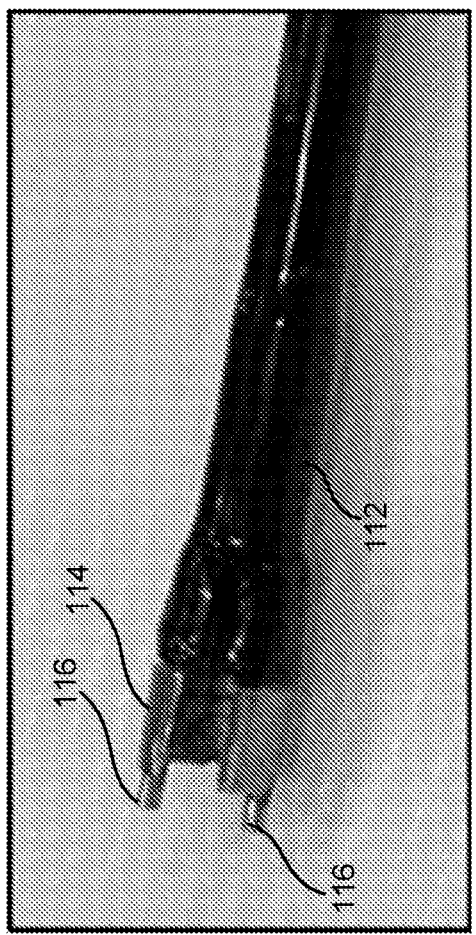

With reference to FIG. 11B-11E, the alignment feature 112 may be disposed over the driveline 110 and is configured to push against the pump 24 during positioning of the ventricular device system 100. The alignment feature 112 in guiding the system during placement of the ventricular assist device 10 (FIG. 11A). For example, the alignment feature 112 may assist in guiding the ventricular assist device 10 as the sheath 102 (FIG. 11A) is retracted. As illustrated in FIGS. 11C and 11D, the alignment feature 112 may include a catheter tip 114, which may divided into two halves each including a pin 116, as illustrated in FIG. 11C. It is contemplated that the catheter tip 114 may be formed from a polymer or metal. The pins 116 of the catheter tip 114 may couple to indentations 118 formed in the pump 24, as illustrated in FIG. 11E, to assist in rotating and directing the placement of the system 100. To remove the alignment feature 112, the catheter tip 114 may be split to peel the alignment feature 112 away from the driveline 110.

Referring now to FIGS. 12A-13B, the pump 24 is configured as a percutaneous ventricular assist device to provide endovascular mechanical circulatory support of either the right or left portions of the heart for up to approximately 30 days. As described herein, the pump 24 assists the right portion of the heart, but it is contemplated that a similar execution may be performed for the left portion. The pump 24 is configured to pump a blood volume from the inferior vena cava, where the pump 24 is anchored, through the cannula 12 into the pulmonary artery. The ventricular assist device 10 is configured to bypass the right ventricle by being disposed into the pulmonary artery. The pump 24, as mentioned above, is anchored in the inferior vena cava via the pump anchor 26, variations of which are described below.

Figure 12A:
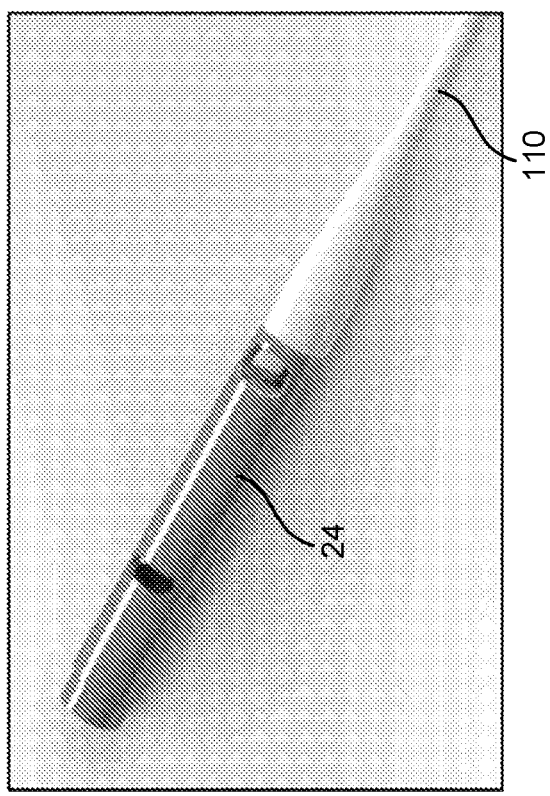
FIG. 12A is a partial perspective view of a pump of a ventricular assist device of the present disclosure.
Figure 12B:
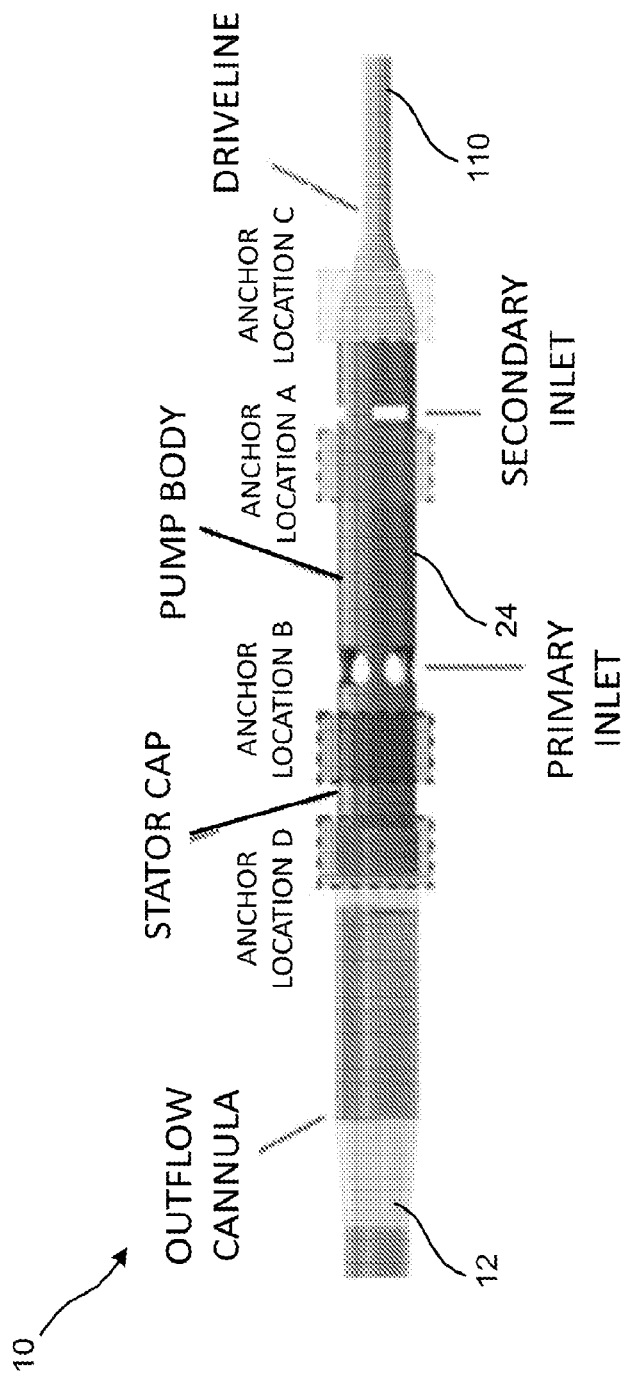
FIG. 12B is a schematic of a pump of a ventricular assist device of the present disclosure indicating potential placements of a pump anchor.
Figure 13B:
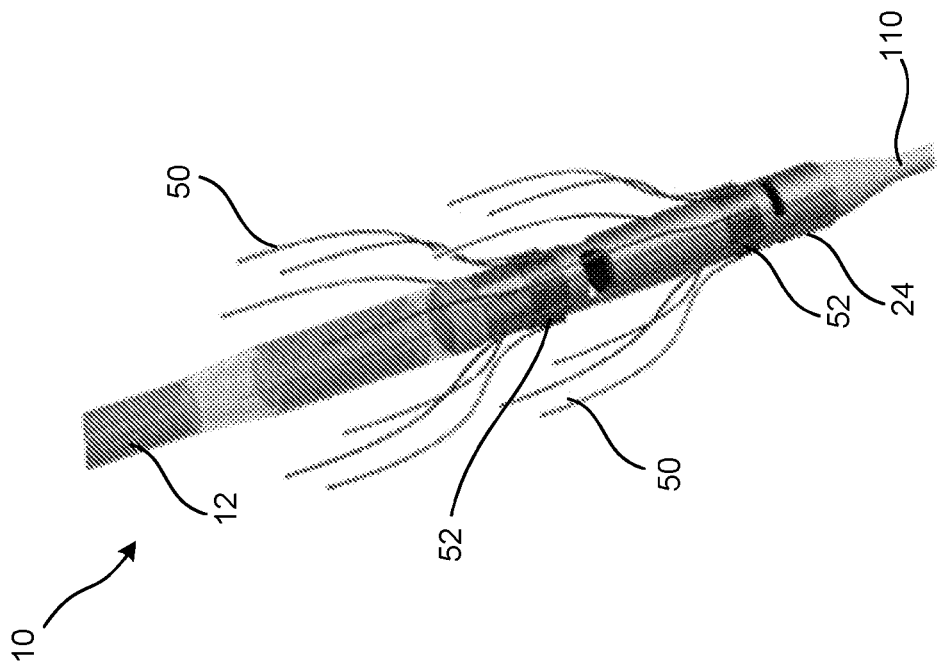
FIGS. 13A and 13B are perspective views of a pump with first and second pump anchors of the present disclosure.
Figure 13A:
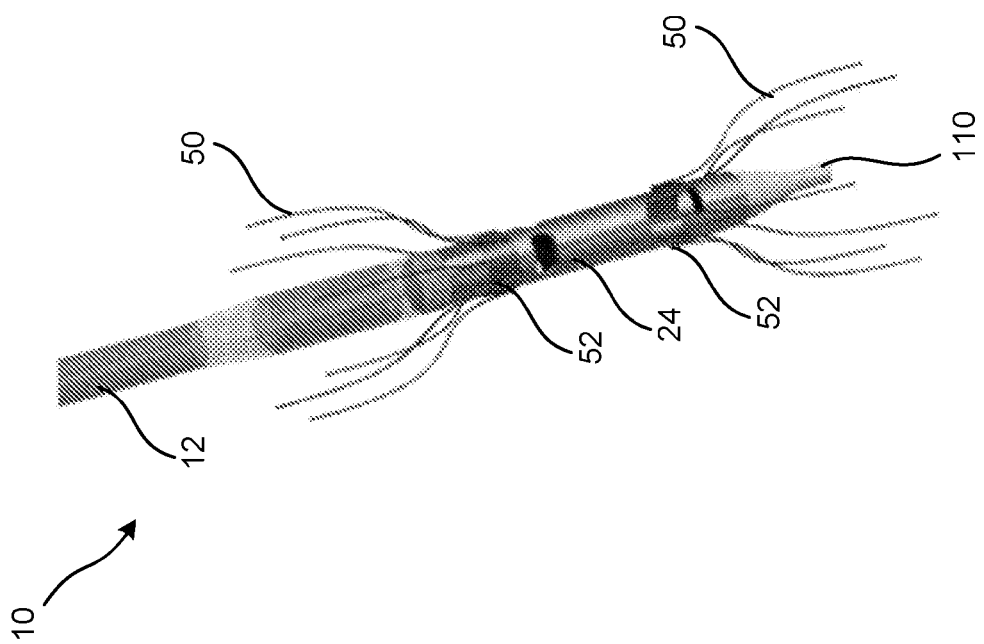
Figure 13C:
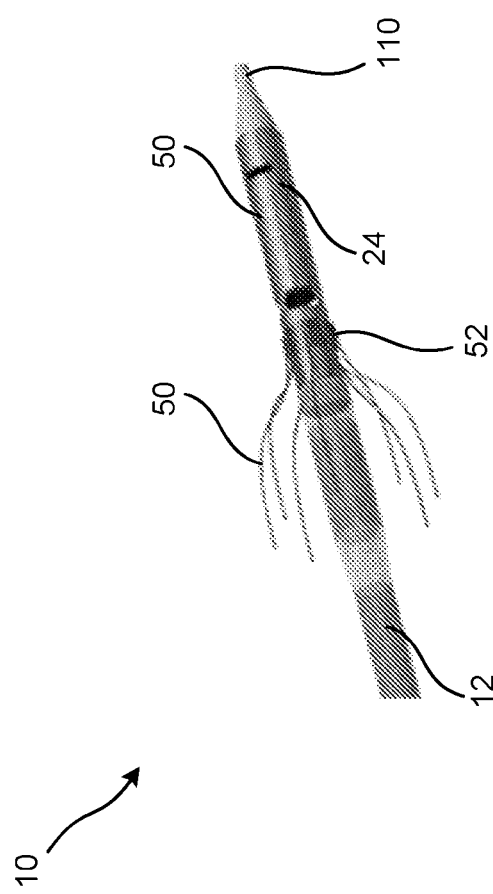
FIG. 13C is a partial perspective view of a pump with a single pump anchor of the present disclosure.

The pump anchor 26 may be positioned at various locations along the pump 24. For example, FIG. 12B illustrates four potential locations along the pump 24 at which the pump anchor 26 may be positioned. Alternate positioned along the ventricular assist device 10 may also be contemplated, such that the positions illustrated in FIG. 12B are by example only and not to be limiting examples. The pump anchor 26 may advantageously minimize frictional movement relative to the inferior vena cava vessel walls, minimize potential thrombus formation, and stabilize radial and axial movement of the pump 24 within the inferior vena cava. It is contemplated that the pump anchor 26 may be positioned proximate the driveline 110 and/or the cannula 12. By way of example, not limitation, the pump anchor 26 may include a first pump anchor 26a and a second pump anchor 26b, such that the first pump anchor 26a may be coupled to the pump 24 proximate the cannula 12 and the second pump anchor 26b may be coupled to the pump 24 proximate the driveline 110. As illustrated in FIG. 13A, the first and second pump anchors 26a, 26b extend in opposing directions. Stated differently, FIG. 13A illustrates the first pump anchor 26a extending toward the cannula 12, and the second pump anchor 26b extending toward the driveline 110. In an alternate implementation, the first and second pump anchors 26a, 26b may extend in the same direction. For example, FIG. 13B illustrates the first and second pump anchors 26a, 26b extending toward the cannula 12. It is also contemplated that both the first and second pump anchors 26a, 26b may extend toward the driveline 110.

Figure 14A:
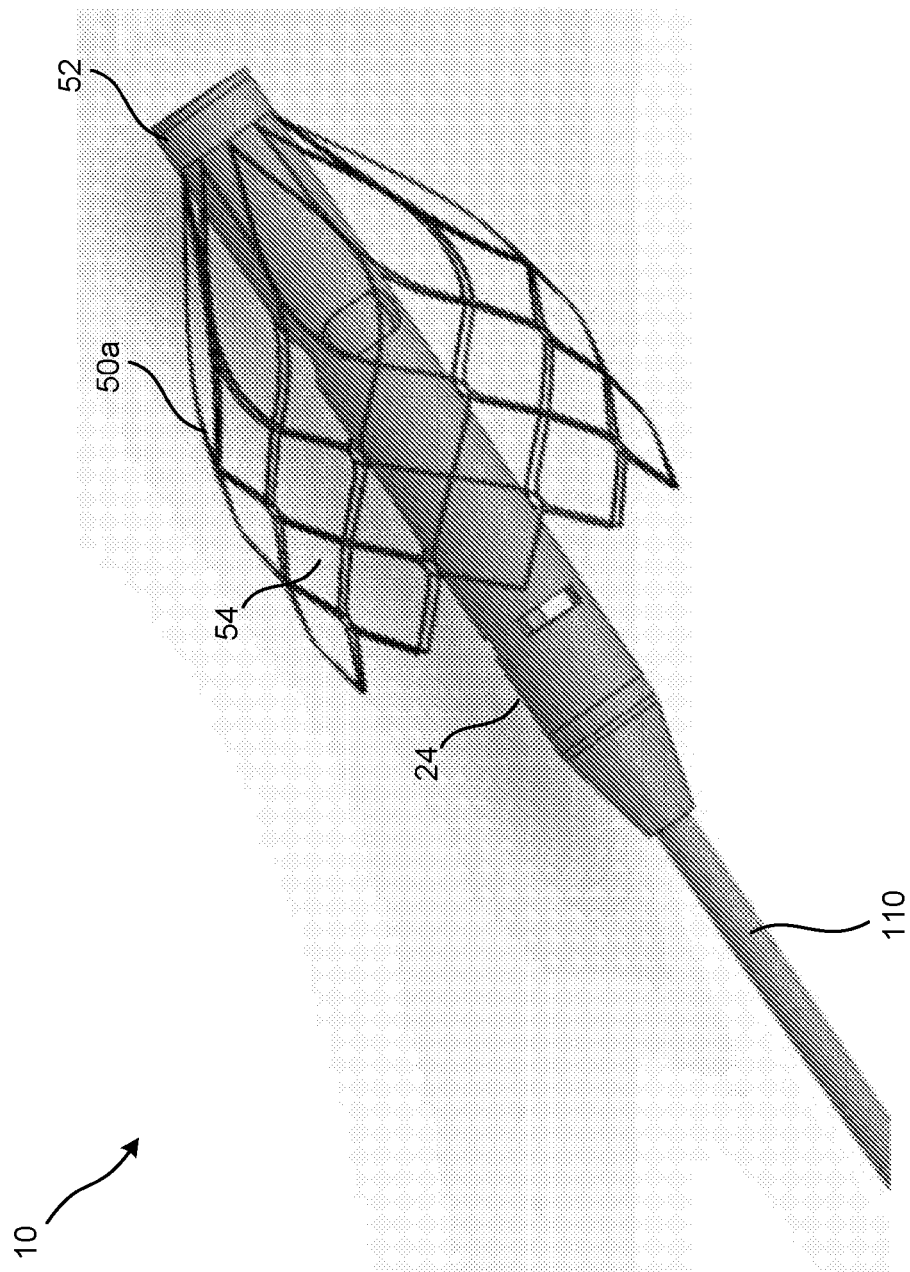
FIGS. 14A and 14B are perspective views of a pump anchor of the present disclosure.
Figure 16A:
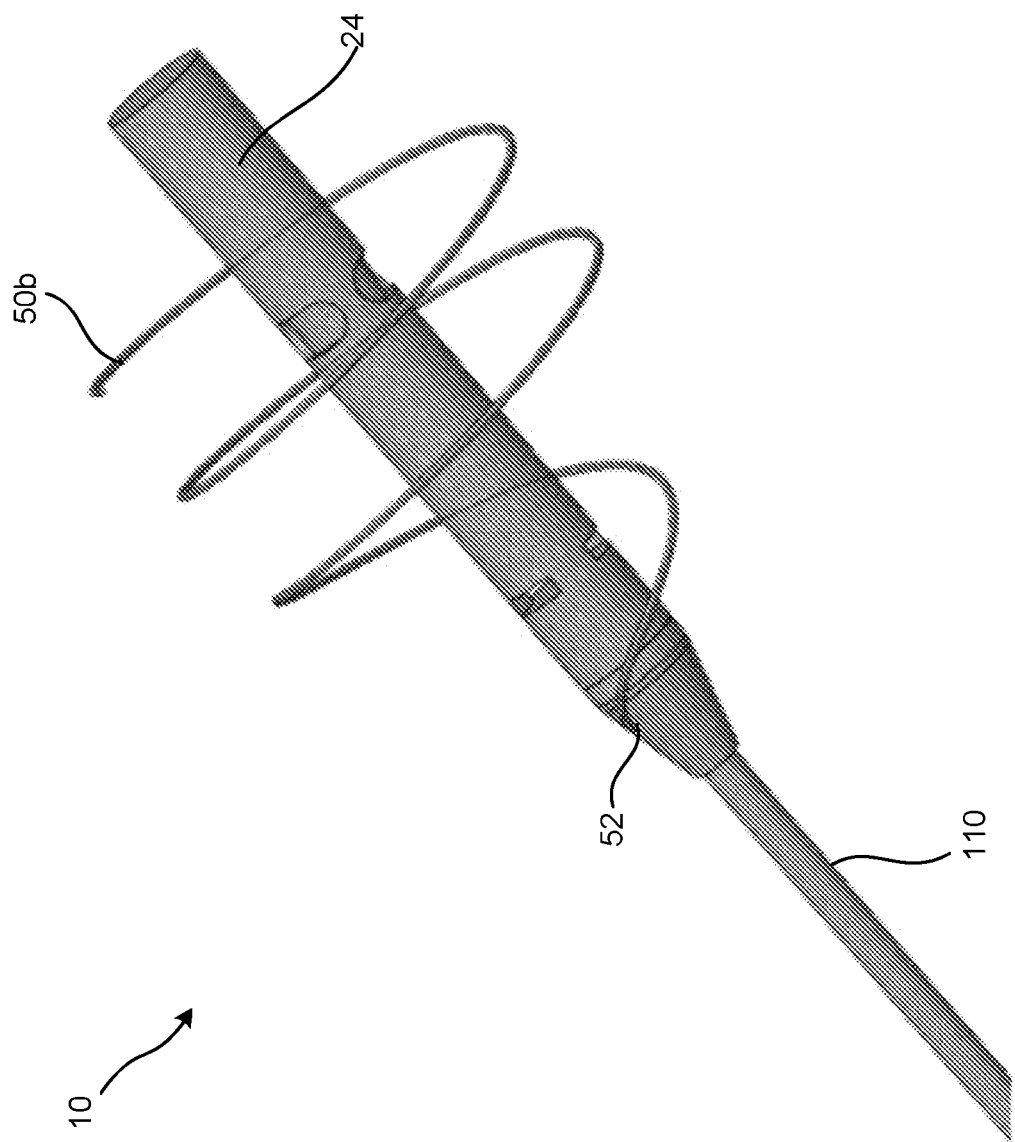
FIGS. 16A and 16B are perspective views of a pump anchor of the present disclosure.

The pump anchor 26 may include a plurality of extensions 50 that extend from an attachment portion 52. For example, each of the first and second pump anchors 26a, 26b may include both the attachment portion 52 and the plurality of extensions 50, as illustrated in FIGS. 13A and 13B. As generally mentioned above, the plurality of extensions 50 of the first pump anchor 26a may extend toward the cannula 12, and the plurality of extensions 50 of the second pump anchor may extend away from the cannula 12. It is also contemplated that alternate configurations of the pump anchor 26 may include an extension body 50a and/or a single extension 50b, as illustrated in FIGS. 14A and 16A, respectively. The pump anchor 26 is formed from a generally flexible material, such that the pump anchor 26 may be collapsed by the sheath 102 during placement and install of the ventricular assist device 10. The pump anchor 26 is operable between the retracted position and the deployed position. For example, when the sheath 102 is disposed around the pump anchor 26, the pump anchor 26 is in the retracted position, and the pump anchor 26 is in the deployed position when the sheath 102 is removed from the ventricular assist device 10. It is also contemplated that the pump anchor 26 may translate between the retracted and deployed positions while being free from engagement with the sheath 102, as described below.

With reference now to FIGS. 14A-15B, the pump anchor 26 is illustrated with the extension body 50a extending from the attachment portion 52. Stated differently, the plurality of extensions 50 may define an interconnected net 50a disposed around the pump 24. In this configuration, the extension body 50a is depicted as having a net configuration, such that a plurality of apertures 54 are defined within the extension body 50a. The pump anchor 26 may be formed from a nickel-titanium (e.g., Nitinol) tube and is attached at an exterior surface of the pump 24. The pump anchor 26 is configured to expand and subsequently radially collapse around the pump 24 when the sheath 102 is deployed. When the sheath 102 is removed, the pump anchor 26 returns to the expanded state. The plurality of apertures 54 of the pump anchor 26 may assist in maintaining fluid communication within the inferior vena cava (FIG. 1A) while anchoring the ventricular assist device 10 within the inferior vena cava (FIG. 1A). The pump anchor 26 may have greater or fewer apertures 54 than those illustrated. For example, an increased number of apertures 54 may assist as a thrombus filter while also providing additional radial force. As mentioned above, the extension body 50a of the pump anchor 26 may extend toward (FIG. 14A) or away from (FIG. 14B) the driveline 110. The pump anchor 26 may also be coupled to the driveline 110, such that the pump anchor 26 may extend over the driveline 110, as depicted in FIG. 14C. The positioning of the pump anchor 26 along the driveline 110 may minimize the overall diameter of the system 100, which may be advantageous during implantation of the ventricular assist device 10.

Figure 14B:
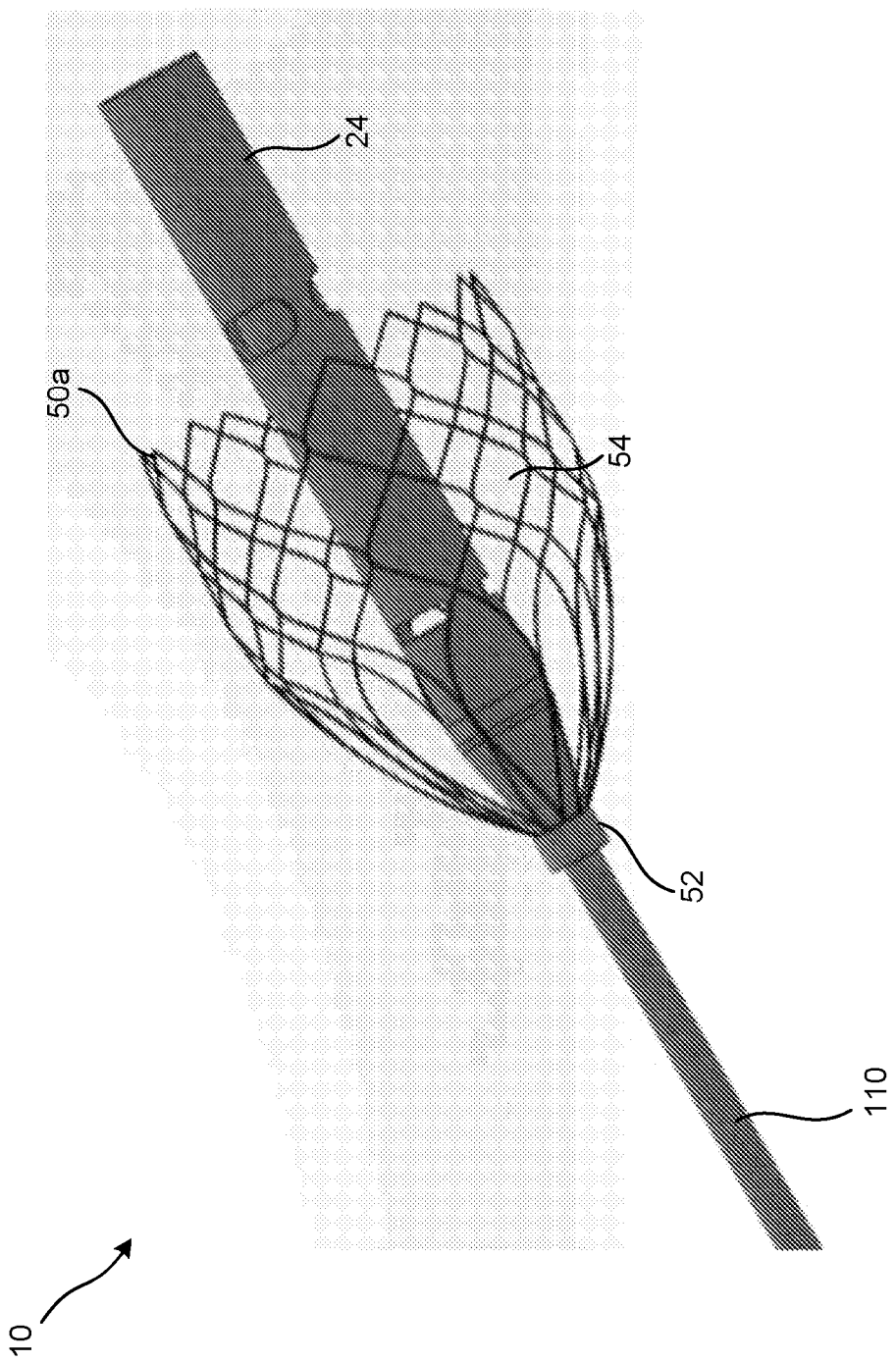
Figure 14C:
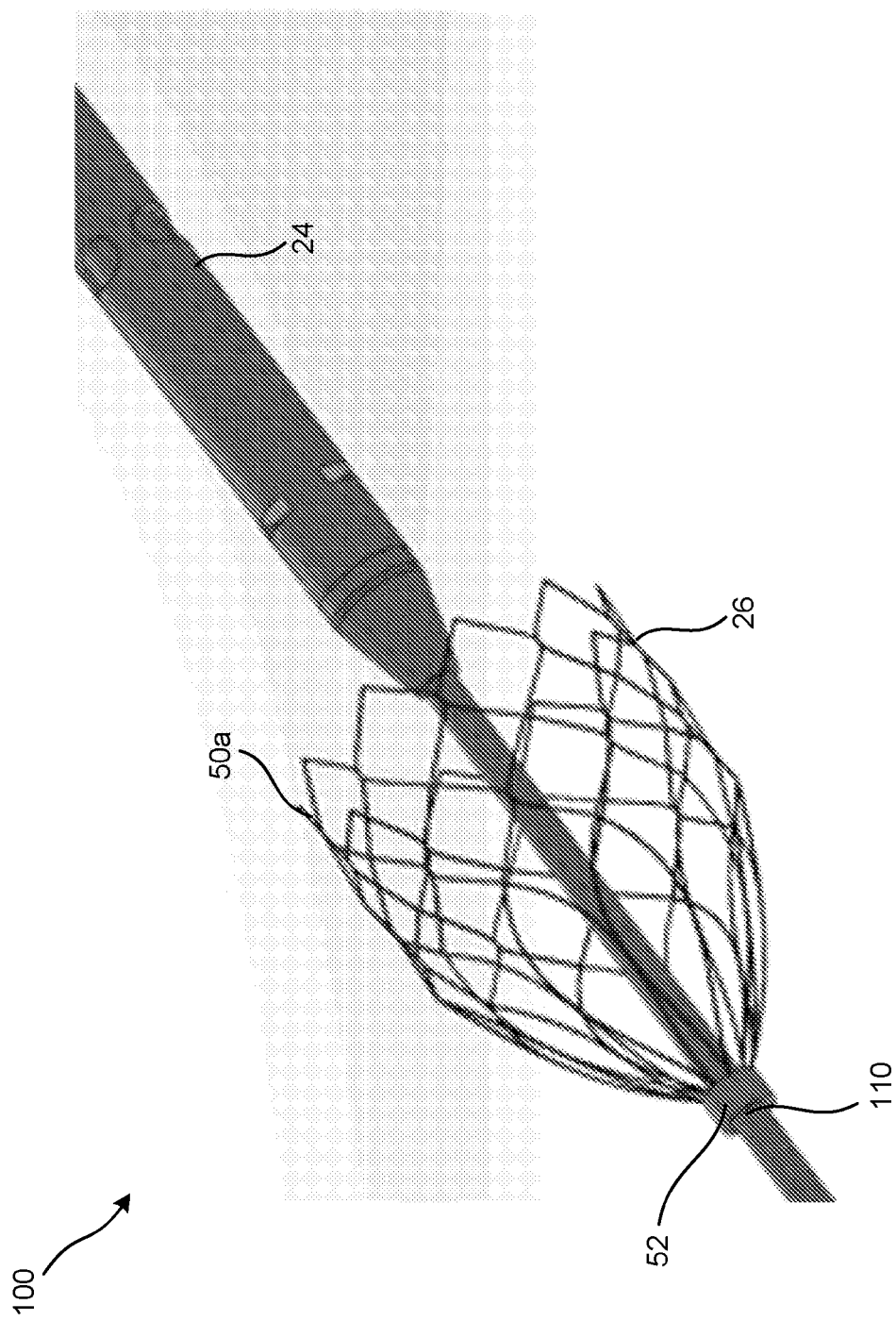
FIG. 14C is a partial perspective view of a pump anchor of the present disclosure attached to a driveline.
Figure 15A:
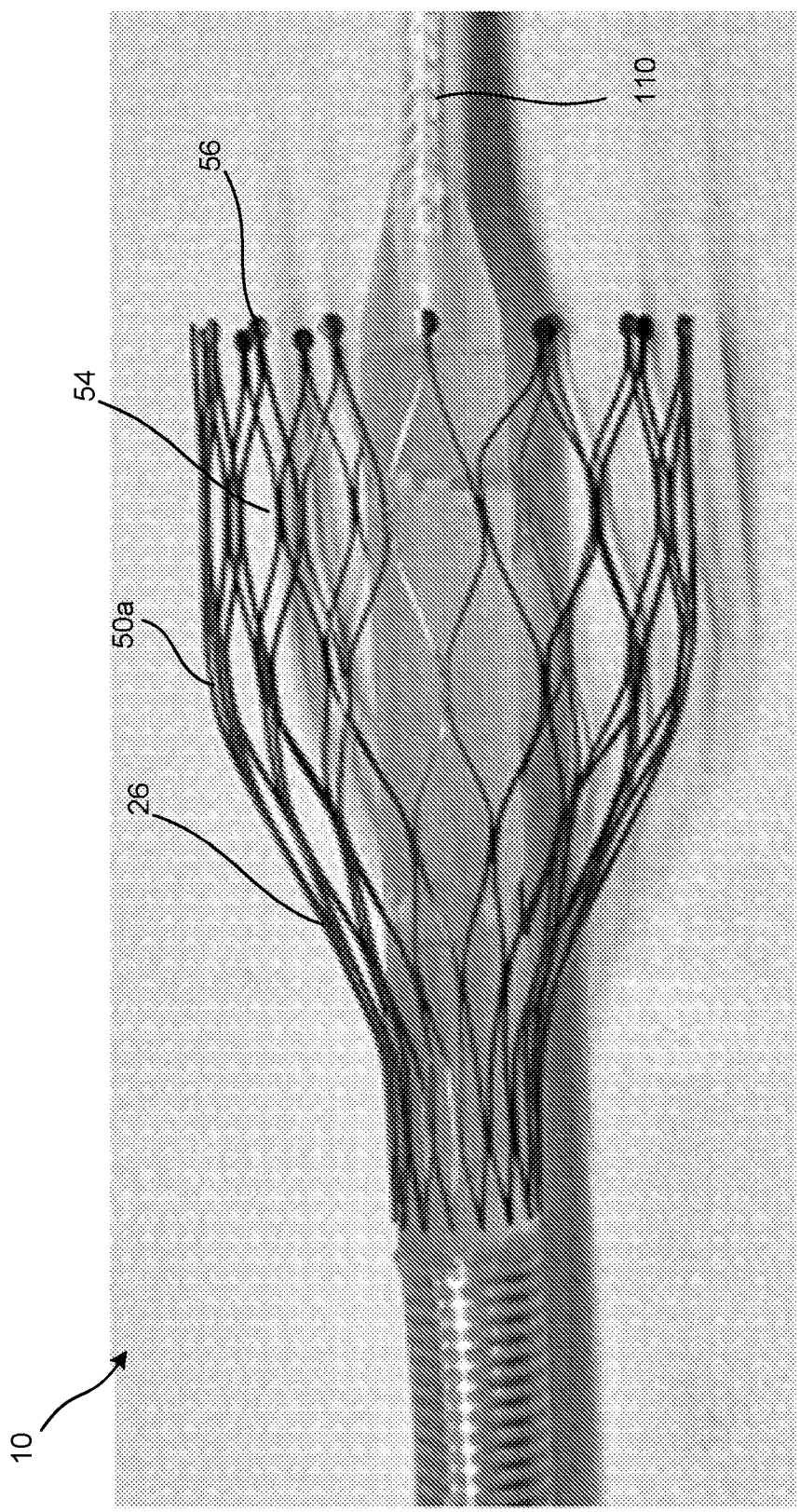
FIG. 15A is an enlarged partial perspective view of a pump anchor of the present disclosure having a net configuration.
Figure 15B:
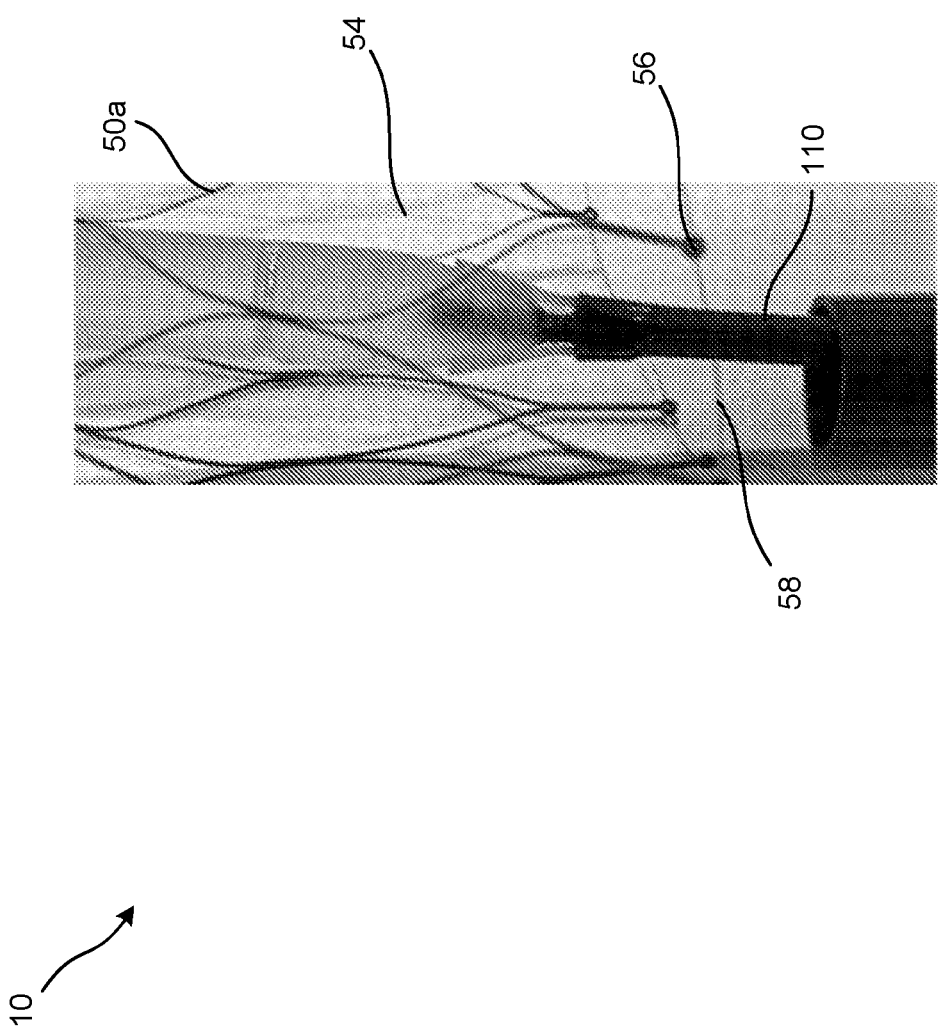
FIG. 15B is an enlarged partial perspective view of a pump anchor of the present disclosure with eyelets and a wire.
Figure 15C:
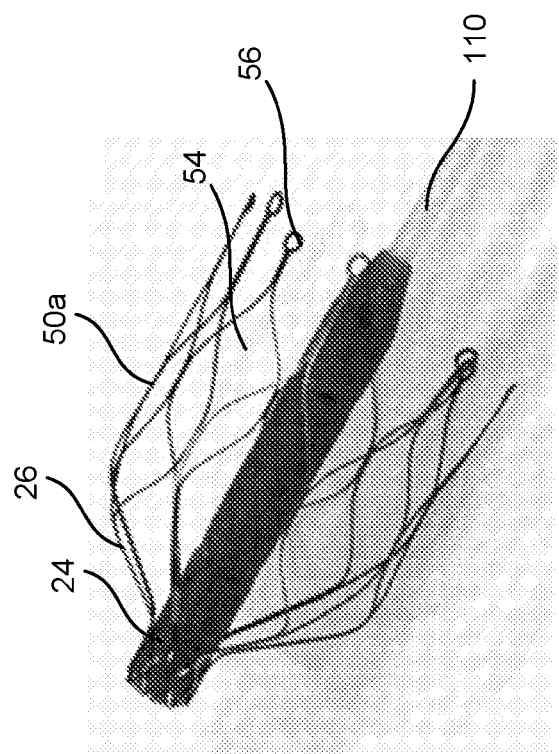
FIG. 15C is a perspective view of a pump anchor of the present disclosure disposed over a pump and including a net configuration and eyelets.

As illustrated in FIG. 15A, the extension body 50a may include a plurality of eyelets 56 and a wire 58 at an opposing end from the attachment portion 52. The plurality of eyelets 56 may provide an alternate method of retracting and deploying the pump anchor 26, such that the eyelets 56 may be proximate one another in the retracted position of the pump anchor 26. For example, the wire 58 may be drawn to draw the eyelets 56 close to one another and retracting the pump anchor 26 away from the walls of the inferior vena cava 202. It is further contemplated that the eyelets 56 may be offset at varying lengths to assist in recapture of the pump anchor 26 by the sheath 102. Alternatively, the pump anchor 26 may have a uniform edge, as depicted in FIGS. 14A and 14B. Although illustrated with respect to the extension body 50a, it is contemplated that the eyelets 56 and wire 58 may be incorporated and utilized in any of the pump anchor 26 configurations described herein.

Figure 16B:
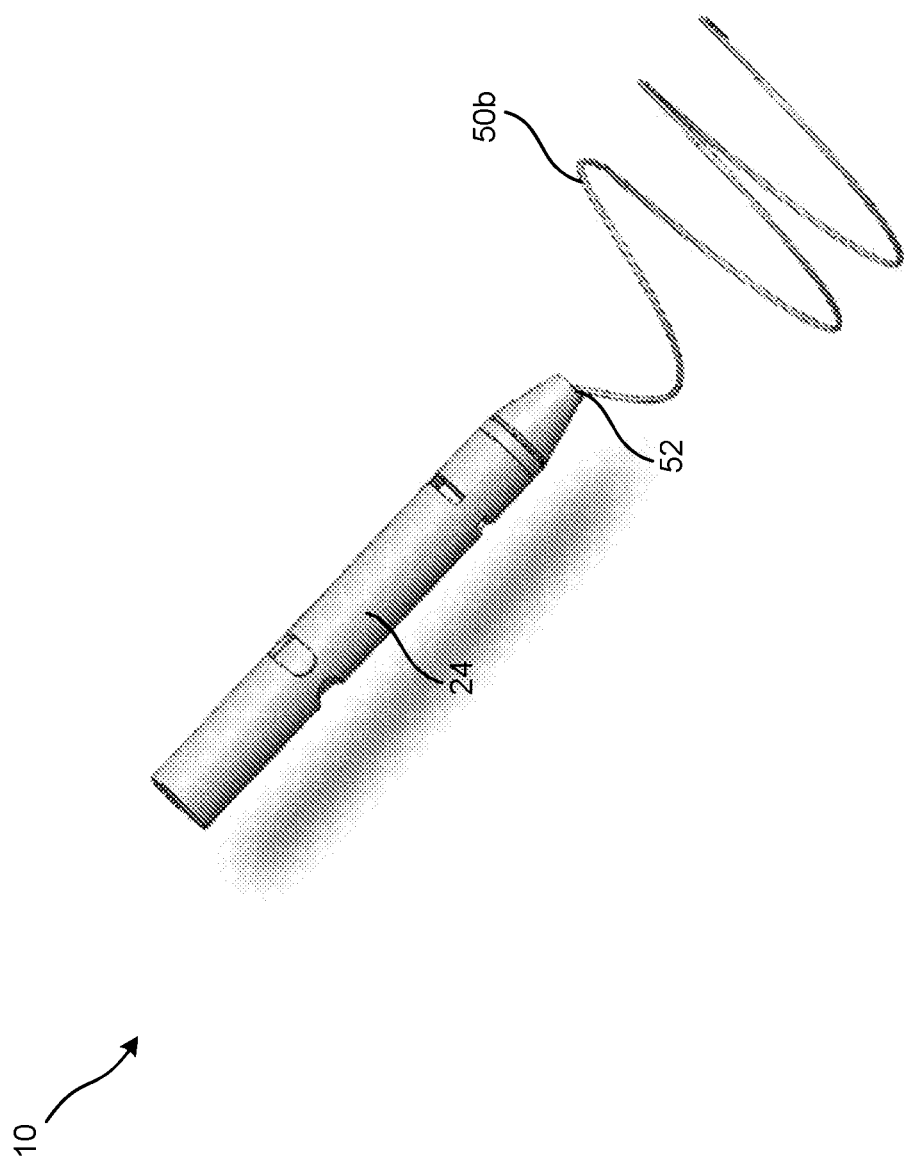

Referring to FIGS. 16A and 16B, the pump anchor 26 is illustrated with the single extension 50b. In this configuration, the single extension 50b of the pump anchor 26 has a spiral configuration. The spiral configuration may assist in providing flexibility in multiple directions for the ventricular assist device 10, such that the pump anchor 26 may be generally compressed along the pump 24 while retaining a general circumference. It is also contemplated that the single extension 50b may be wound around the pump 24 to expand and retract about the pump during positioning and install of the ventricular assist device 10. In any of the configurations of the pump anchor 26 illustrated in FIGS. 13A-16B, it is contemplated that the pump anchor 26 is deployed within the inferior vena cava 202 to retain the ventricular assist device 10 in the desired position during a treatment period, described in more detail below.

Figure 1B:
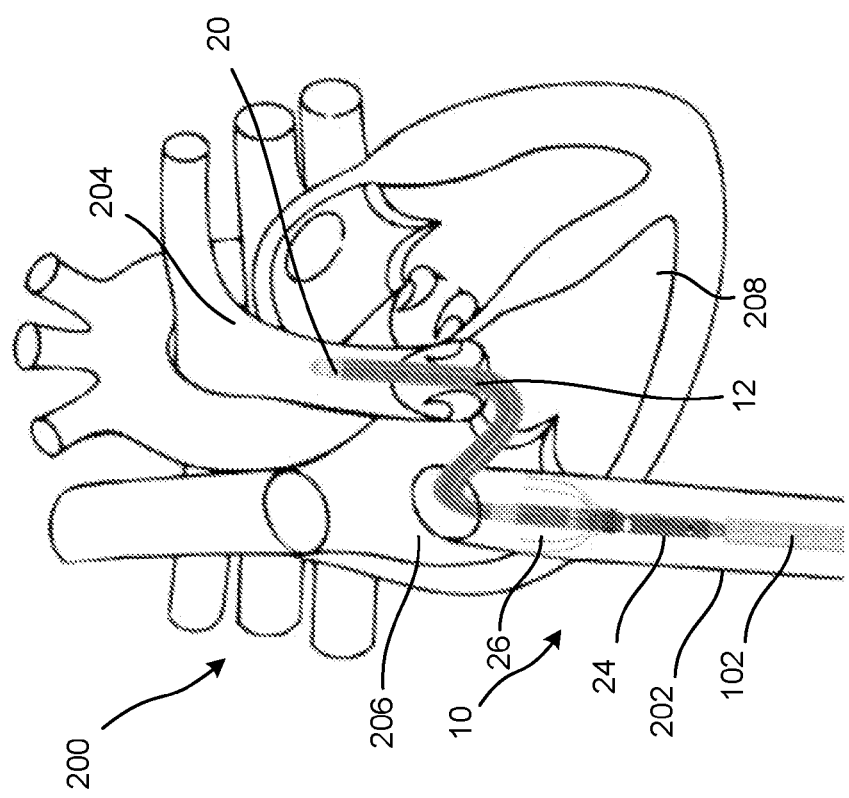
Figure 17:
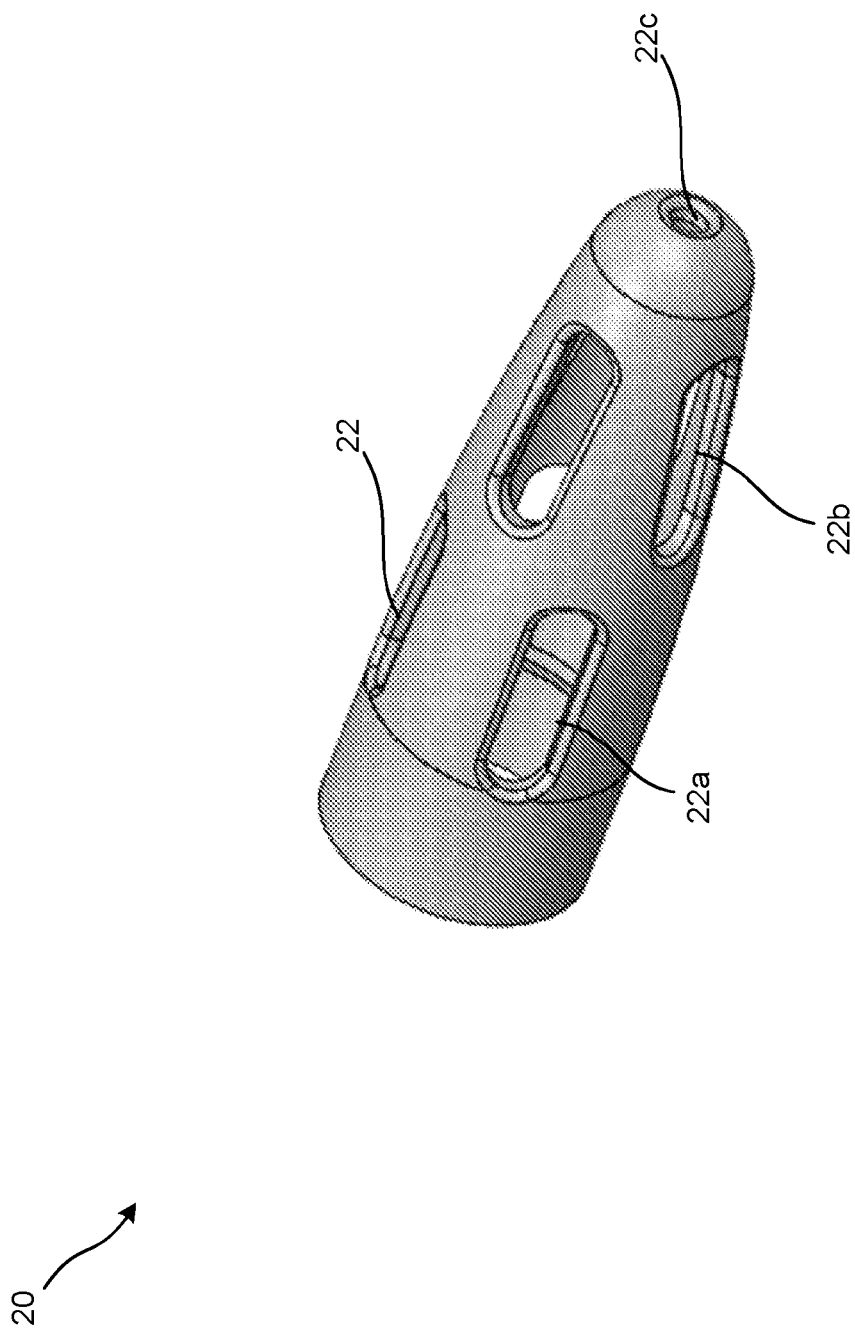
FIG. 17 is a perspective view of a tip of a ventricular assist device of the present disclosure.

With reference now to FIGS. 17-19A, the tip 20 of the cannula 12 may have a single opening 22 on each side 70 of the tip 20, as mentioned above, and/or may have multiple openings 22, as illustrated in FIG. 17, around a circumference of the tip 20. It is generally contemplated that the tip 20 may have a lantern or lighthouse configuration. In one implementation, the lantern configuration is defined by the openings 22 being staggered around the tip 20. For example, a first row 22a of the openings 22 may be offset relative to a second row 22b of the openings 22. The lantern configuration and alignment of the openings 22 may assist in preventing clot formation within the ventricular assist device 10, the tip 20, and the pulmonary artery 204 (FIG. 1B) where the tip 20 is ultimately positioned. Stated differently, the openings 22 assist in providing uniform flow distribution and minimal pressure drop. Additionally, a top opening 22c cooperates with the guidewire 104 (FIG. 8), such that the tip 20 may track over the guidewire 104. In either configuration, the tip 20 has a lower arcuate portion 72 and an upper narrow portion 74. As illustrated in FIGS. 18A-19B, the lower arcuate portion 72 and the upper narrow portion 74 may define a droplet shape of the opening 22. This shape may assist in the transport of fluid exiting the cannula 12 into the pulmonary artery 204 (FIG. 1B). The tip 20 may also include the tip anchor 28, mentioned above, to align and retain the tip 20 in the desired position within the pulmonary artery 204 (FIG. 1B).

Figure 18B:
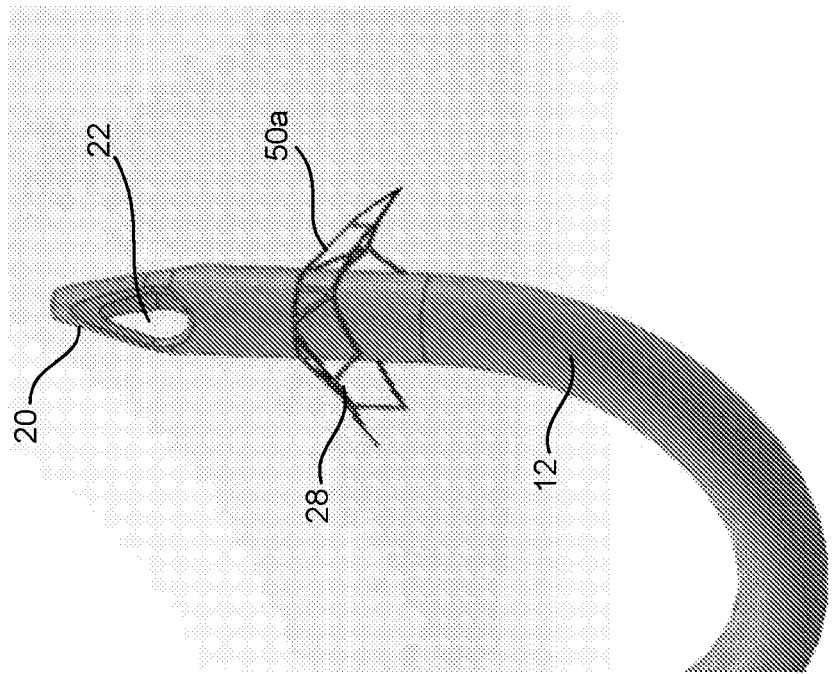
FIGS. 18A and 18B are perspective views of a tip anchor of the present disclosure.
Figure 18A:
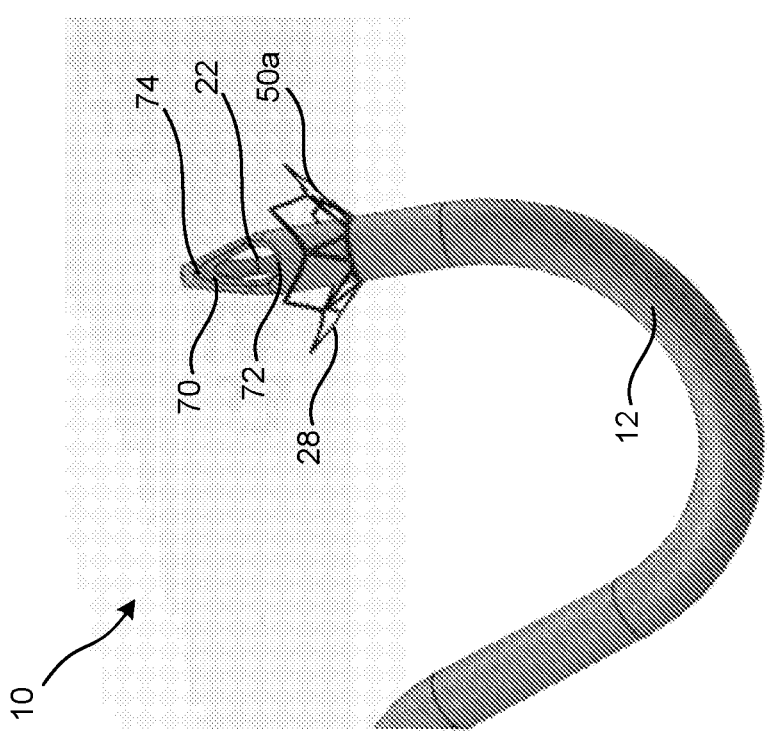

For example, the tip anchor 28 illustrated in FIGS. 18A and 18B has a net configuration similar to the pump anchor 26 illustrated in FIGS. 14A and 14B. The tip anchor 28 of this configuration may be deployed and retracted in a similar manner as described with respect to the pump anchor 26, such that the tip anchor 28 may also include the attachment portion 52 and plurality of extensions 50 extending from the attachment portion and the eyelets 56 and wire 58 at an opposing end from the attachment portion 52. The eyelets 56 and the wire 58 may retract the tip anchor 28 around the tip 20 and/or cannula 12. In one implementation, the pump anchor 26 (FIG. 13A) and the tip anchor 28 may be coupled to the pump 24 (FIG. 13A) and the second end 18 of the cannula 12, respectively, at the respective attachment portions 52. It is generally contemplated that the tip anchor 28 may extend toward either the tip 20 or the cannula 12, and in either configuration, the tip 20 retains the tip 20 in the installed position.

Figure 19A:
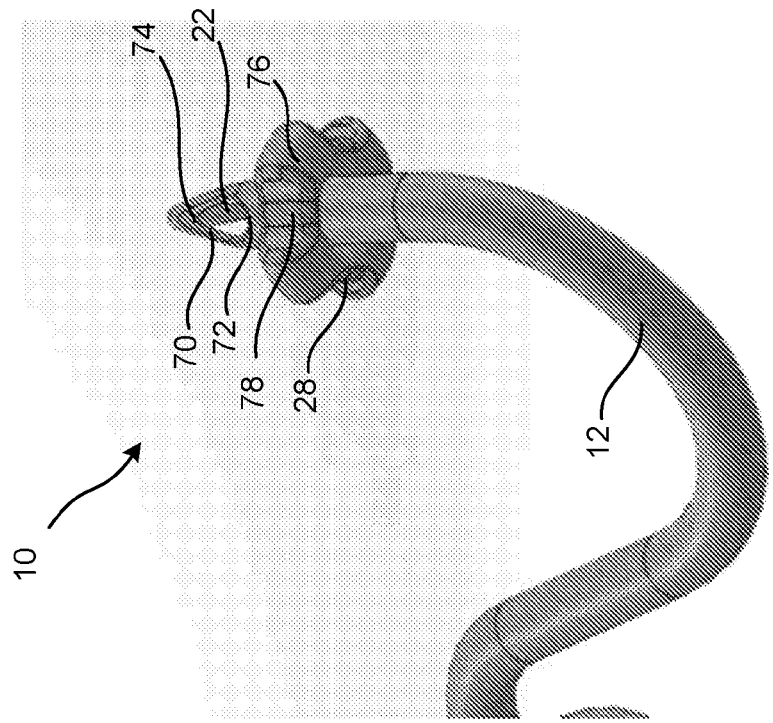
FIGS. 19A and 19B are perspective views of a tip anchor of the present disclosure.
Figure 19B:
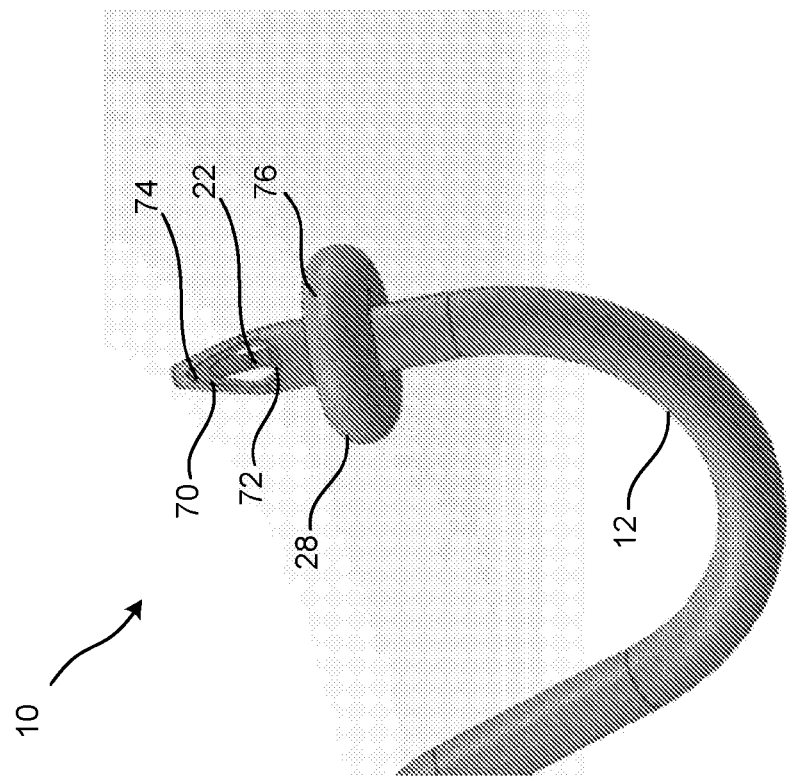

As illustrated in FIGS. 19A and 19B, the tip anchor 28 is illustrated as having a balloon configuration. In this example, the tip anchor 28 may be deployed by inflation of an inflatable body 76 about the cannula 12 at the base of the tip 20. The inflatable body 76 has an expanded position and a contracted position, such that the inflatable body 76 is in the contracted position as the ventricular assist device 10 is being installed and translates to the expanded position to at least partially secure the ventricular assist device 10 within the pulmonary artery 204 (FIG. 1B). The inflated tube 76 has a circumference that assists in aligning the ventricular assist device 10 within the pulmonary artery 204 and heart 200 more generally. For example, it is contemplated that the inflation of the inflatable body 76 may center the tip 20 within the pulmonary artery 204. FIG. 19B illustrates another configuration of the inflatable body 76. In this alternate configuration, the inflatable body 76 defines a plurality of recesses 78. As illustrated in FIG. 19B, the recesses 78 align with the opening 22 defined by the tip 20, which promotes ease of fluid flow around the ventricular assist device 10 and, specifically, the tip 20. While fluid may pass through the ventricular assist device 10, it is also contemplated that the ventricular assist device 10 may promote fluid flow between the inferior vena cava 202 (FIG. 1B) and the pulmonary artery 204 (FIG. 1B) to assist in performance of the heart 200 (FIG. 1B).

Referring now to FIGS. 20A-21C, a delivery device 120 is illustrated as coupled to the ventricular assist device 10 for installation in the heart 200. The delivery device 120 may be part of the ventricular assist system 100 or may be separate from the system 100. The delivery device 120 is configured to deliver and remove the ventricular assist device 10. It is contemplated that the delivery device 120 is configured to extend and retract both the alignment feature 112 and the sheath 102, described above. The delivery device 120 includes an actuator 122 coupled to a handle 124 within a guide channel 126 defined by the handle 124. The guide channel 126 may have a defined pattern that may assist in the operation of the delivery device 120 where visibility of the handle 124 may be impaired. The handle 124 may also include a locking feature 128 configured to prevent movement of the actuator 122 within the guide channel 126. The locking feature 128 is operable between a first, locked position and a second, unlocked position. As illustrated in FIG. 20D, the locking feature 128 extends proximate to the actuator 122 in the first position and extends away from the actuator 122 in the unlocked position. It is further contemplated that the locking feature 128 may be identified with a color to indicate the locked or unlocked state of the locking feature 128. By way of example, not limitation, the portion of the locking feature 128 proximate to the actuator 122 in the first, locked position may be red and the portion extending away from the actuator 122 in the second, unlocked position may be green. It is contemplated that other color combinations may also be utilized to visually depict the locked and unlocked positions of the locking feature 128.

Figure 20D:
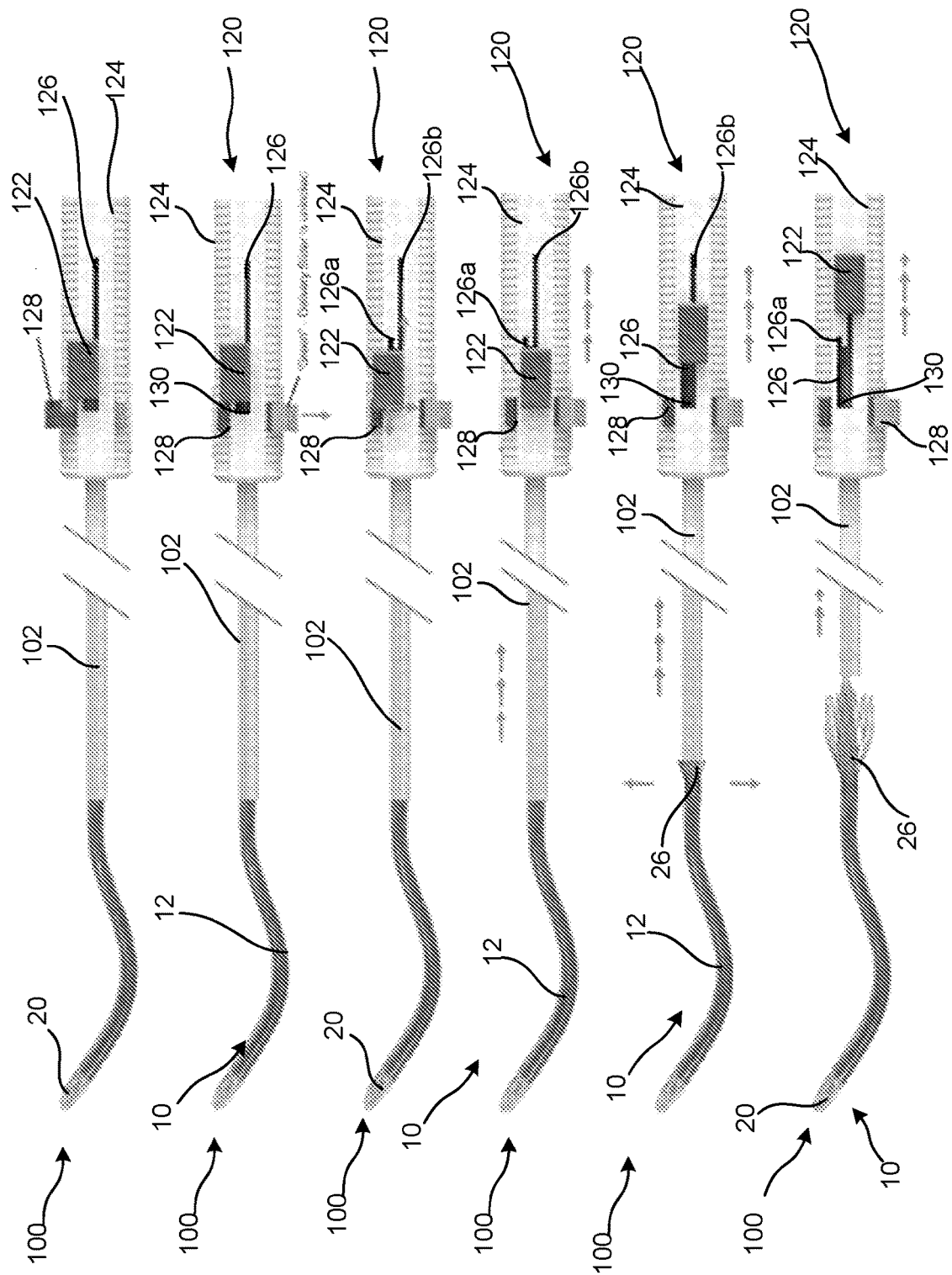
FIG. 20D is a plan view of a ventricular assist system of the present disclosure with stages of retraction of a sheath by a delivery device of the present disclosure.
Figure 20E:
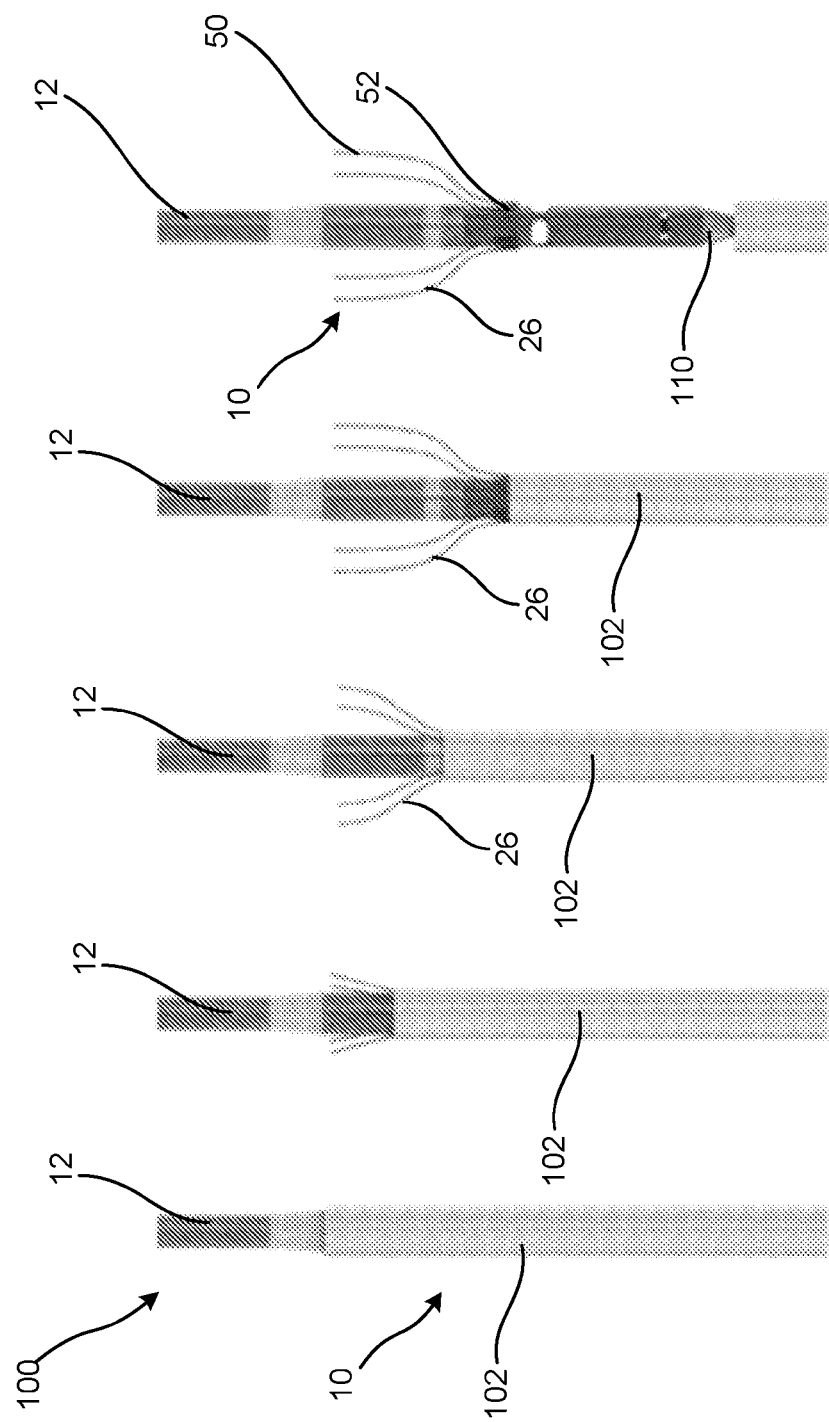
FIG. 20E is a partial elevational view of a sheath being removed from a ventricular assist device of the present disclosure.

In addition, the locking feature 128 includes a cutout 130 that corresponds to the guide channel 126 when the locking feature 128 is in the unlocked position. When the locking feature 128 is in the locked position, the locking feature 128 may block a portion of the guide channel 126 and may otherwise prevent movement of the actuator 122 within the guide channel 126. FIG. 20D illustrates the transition of the locking feature 128 and the actuator 122 relative to the guide channel 126. As the locking feature 128 is transitioned from the locked position to the unlocked position, the cutout 130 of the locking feature 128 is aligned with the guide channel 126, and the actuator 122 may transition within the guide channel 126 along an x-axis and a y-axis. Stated differently, the actuator 122 is positioned in a first channel 126a of the guide channel 126 when the locking feature is in the locked position, and the actuator 122 is translated within the first channel 126a toward the cannula 12 when the locking feature 128 is in the unlocked position. The actuator 122 may then be drawn into a second channel 126 to deploy the sheath 102.

For example, the delivery device 120 is operably coupled to the sheath 102 to extend and retract the sheath 102 about the ventricular assist device 10. It is contemplated that the handle 124 may be generally and/or partially hollow, such that the sheath 102 may be housed within the handle 124 and deployed for installation of the ventricular assist device 10. The delivery device 120 may also deploy the guidewire 104 within the lumen 14 (FIG. 6) of the cannula 12. The delivery device 120 may also retract and/or advance the alignment feature 112, such that the alignment feature 112 may be coupled to the actuator 122 of the handle 124. It is contemplated that the alignment feature 112 may be fixed to the handle 124, such that the handle 124 is configured to push and position the ventricular assist device 10 within the vasculature. The sheath 102 may be coupled to the actuator 122, such that the sheath 102 is configured to slide axially to uncover and cover the device 10 while the delivery device 120 remains stationary. The actuator 122 may be utilized to maneuver the alignment feature 112 during insertion and deployment of the system 100. In one configuration, the sheath 102 may be uncoupled from the delivery device 120 to assist in axial translation of the sheath 102 relative to the guidewire 104. Additionally or alternatively, the delivery device 120 may be free from the alignment feature 112, such that the device 10 may be positioned into place via the driveline 110 connected to the device 10.

FIGS. 20A-20D illustrate a partial view of how the delivery device 120 retracts the sheath 102 from the ventricular assist device 10 once the ventricular assist device is installed. The sheath 102 may form the outermost portion of the delivery device 120. The sheath 102 is configured to collapse and cover the pump anchor 26 and may remain over the pump anchor 26 as the system 100 is advanced into the inferior vena cava 202 (FIG. 21A). Once the system 100 is in place, the sheath 102 may be retracted via the delivery device 120, and the pump anchor 26 is deployed. The removal of the sheath 102, as illustrated in FIGS. 20B and 20C, releases the extensions 50 of the pump anchor 26 to secure the ventricular assist device 10 within the inferior vena cava 202 (FIG. 21A) of the heart 200 (FIG. 21A). FIGS. 21A-21C illustrate, in part, the process in which the delivery device 120 is utilized to reposition the sheath 102 over the ventricular assist device 10, such that the pump anchor 26 is translated from the deployed position to the retracted position. The cannula 12 may be retracted into the sheath 102 and removed from the heart 200 once treatment is complete.

Figure 22:
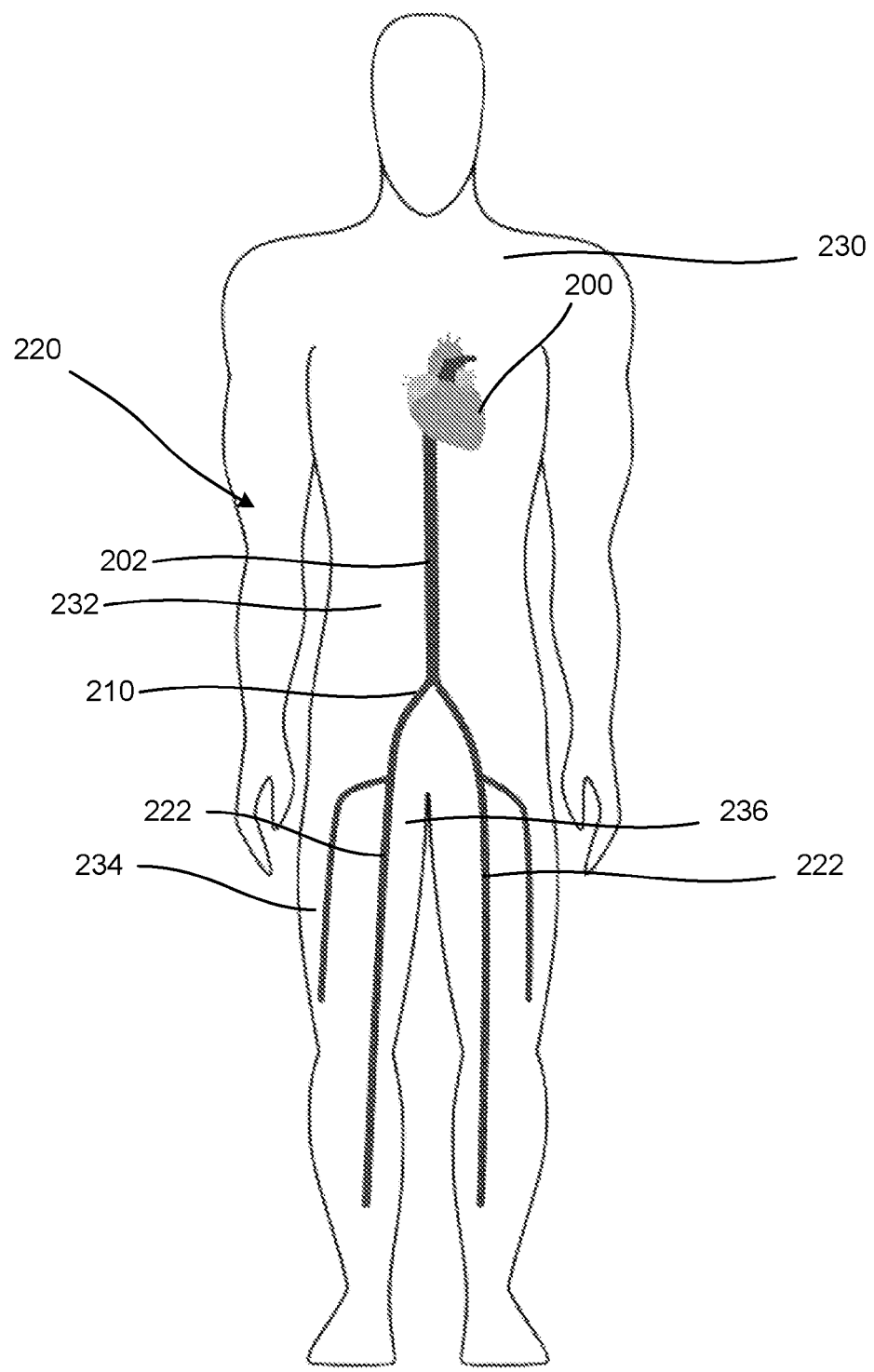
FIG. 22 is a schematic of a circulatory system of a human.
Figures 23A, 23B:
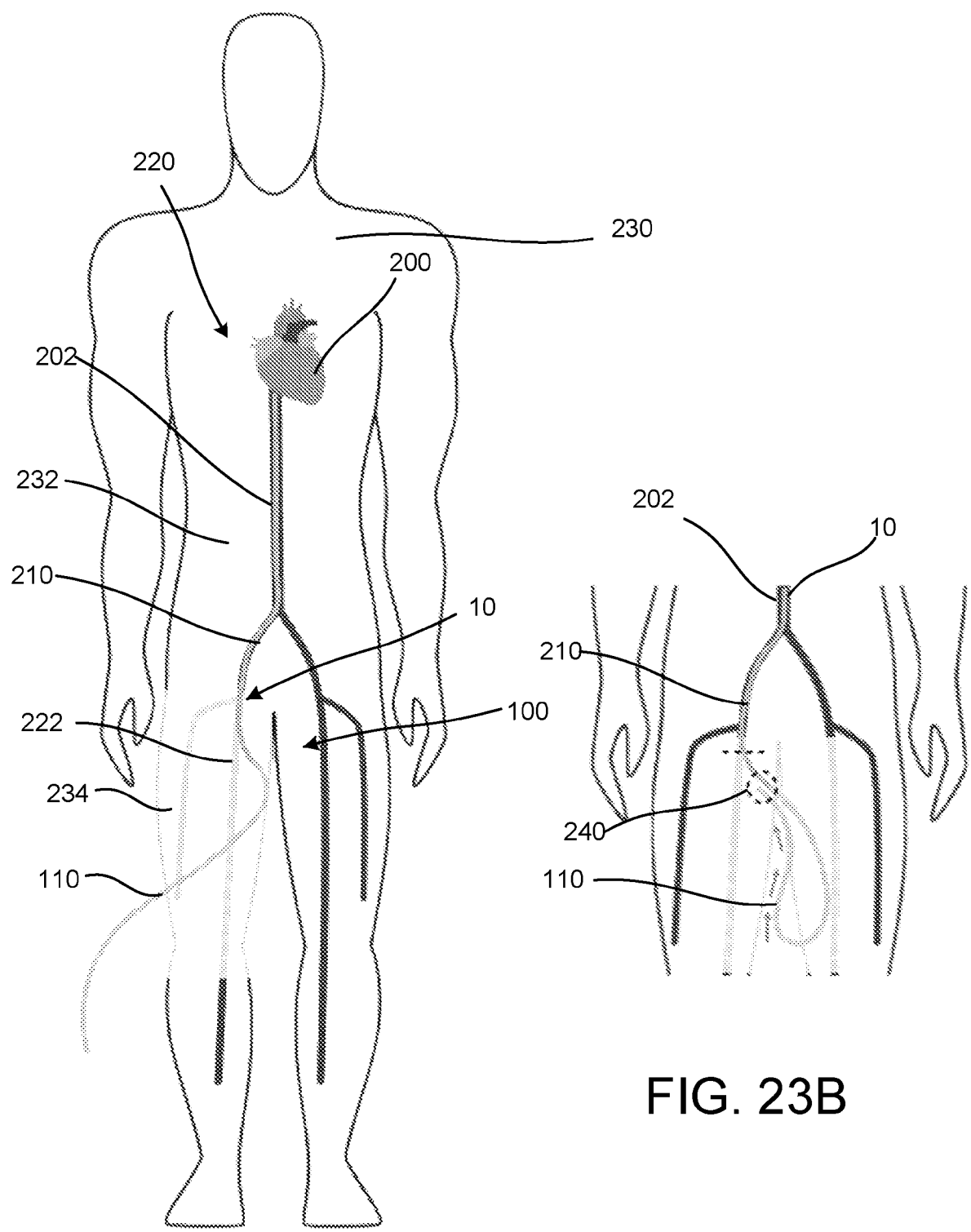
FIGS. 23A and 23B are schematics of the circulatory system of FIG. 22 illustrating an access site and insertion of a ventricular assist system of the present disclosure.
Figures 24A, 24B:
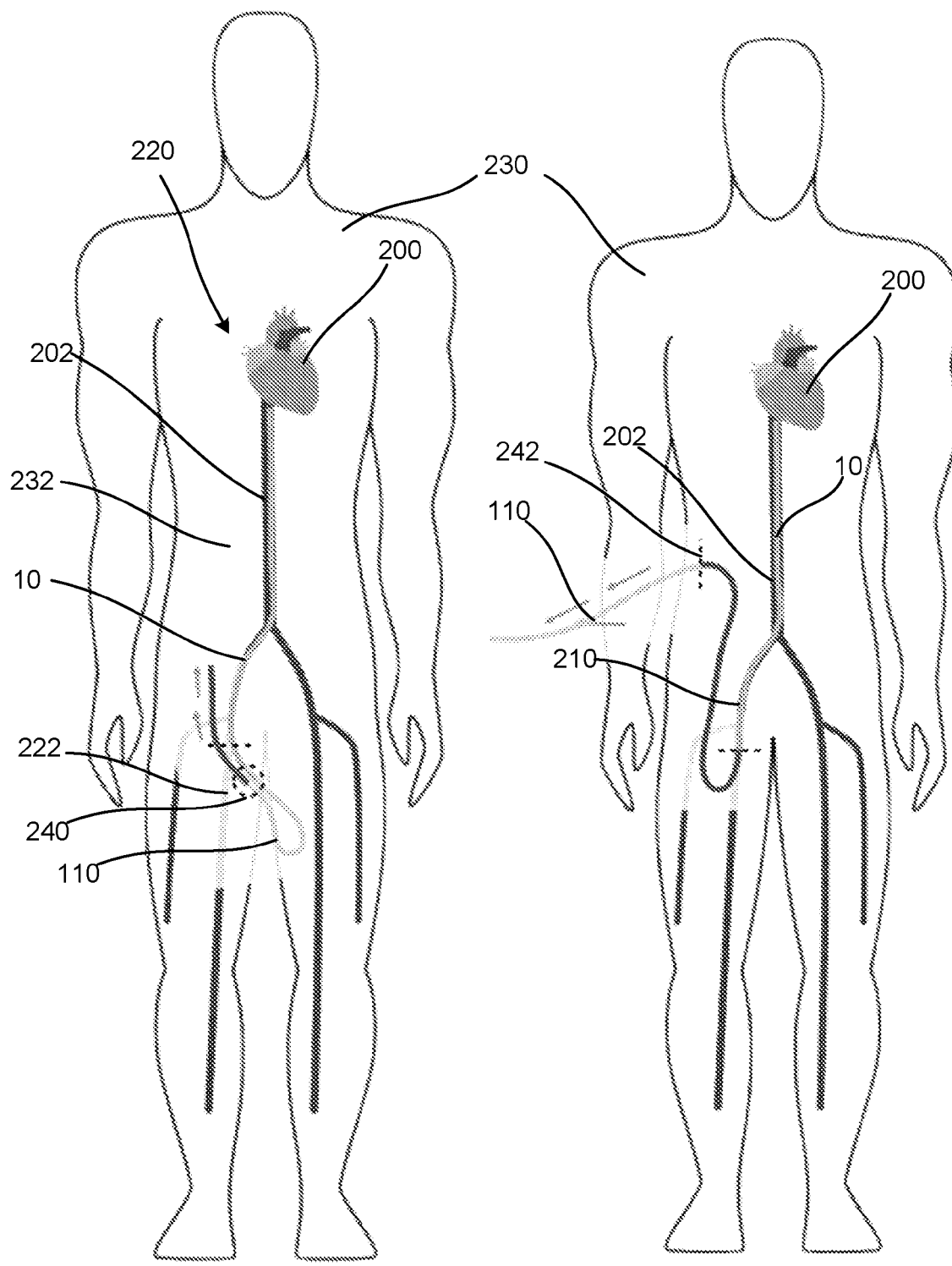
FIGS. 24A and 24B are schematics of the ventricular assist system of FIGS. 23A and 23B and depict subcutaneous repositioning of a driveline of the present disclosure at a treatment site.
Figure 24E:
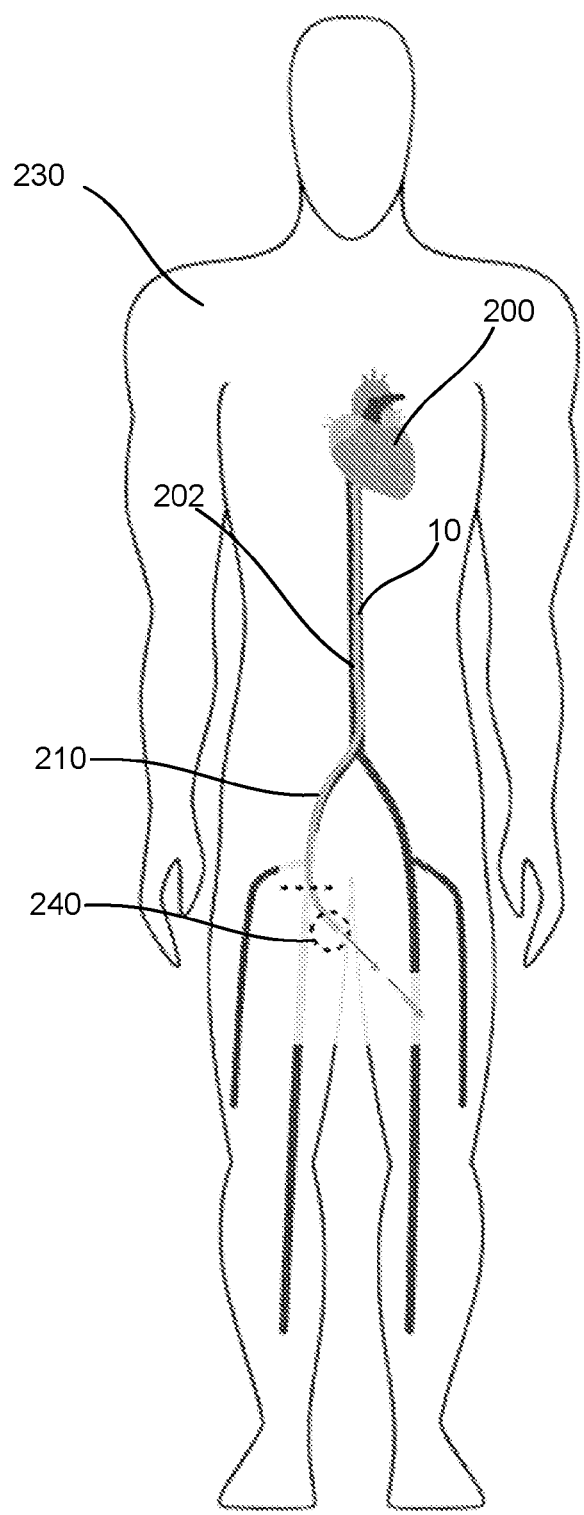
Figure 25C:
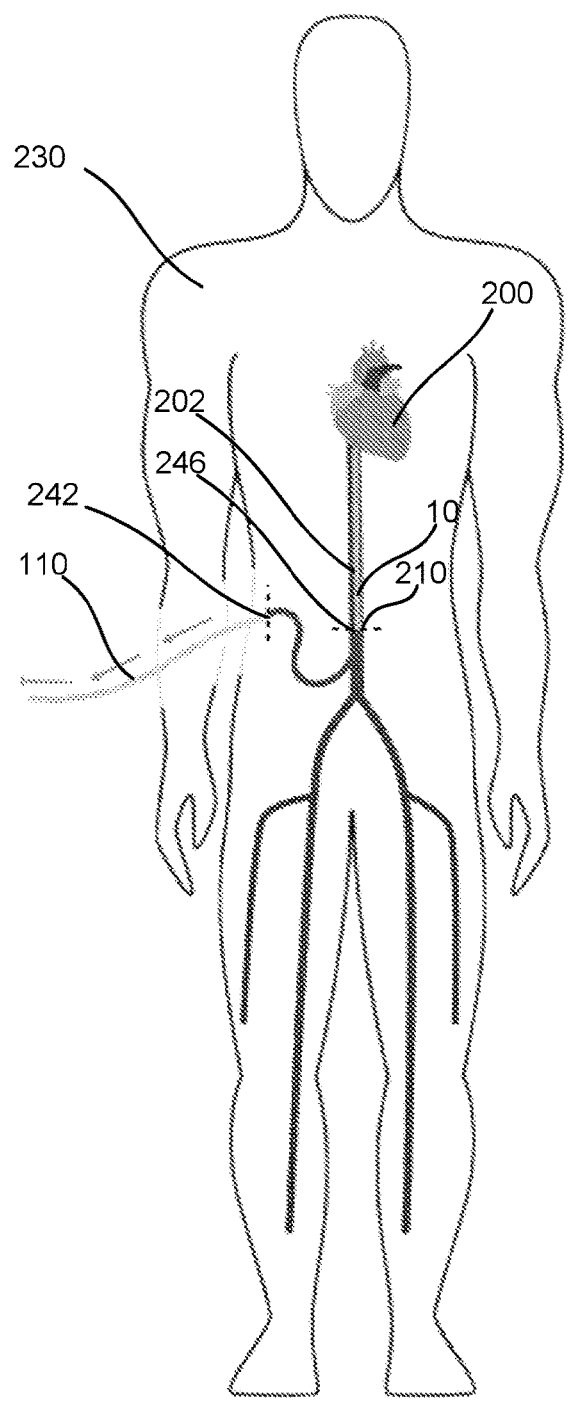
FIGS. 25C-25F are schematics of the ventricular assist system of FIGS. 25A and 25B and depict removal of the ventricular assist system of the present disclosure.
Figure 25D:
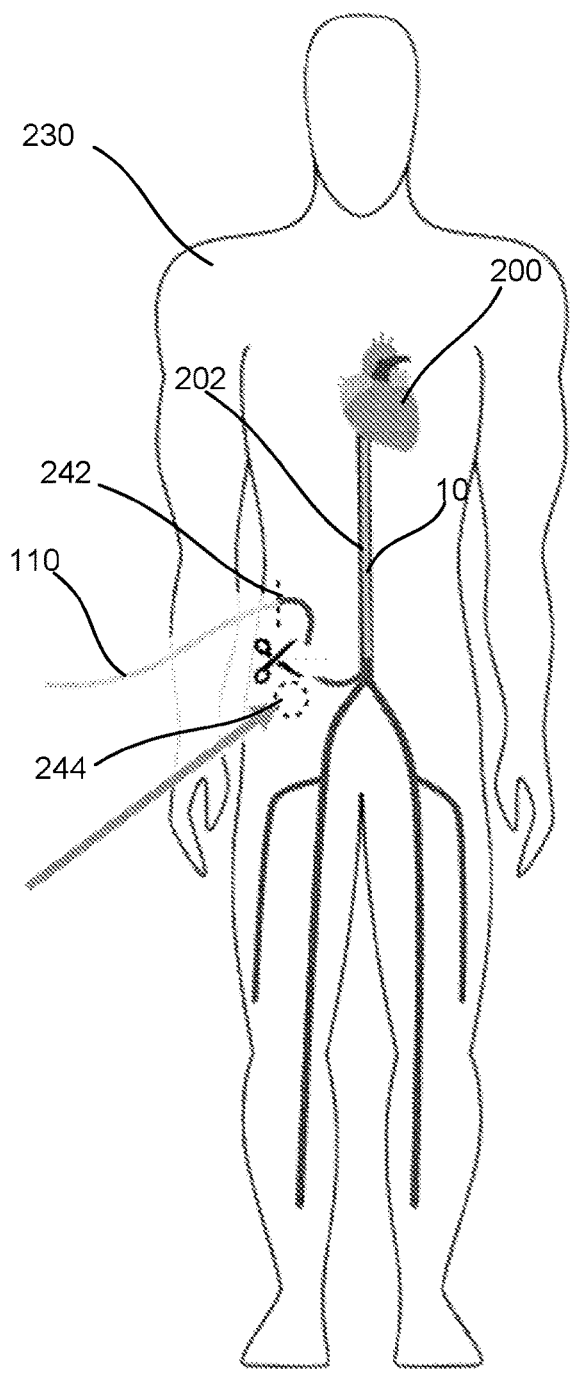
Figure 25E:
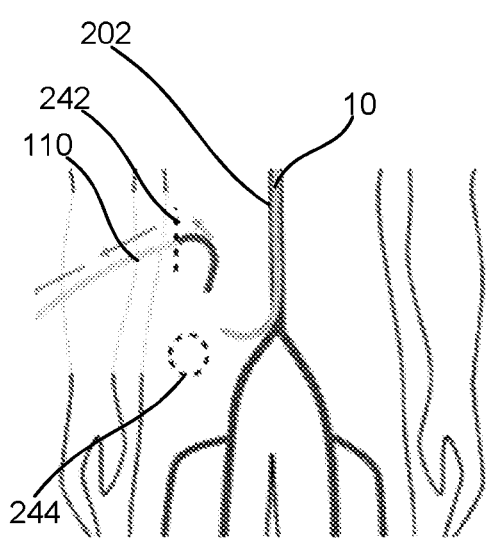
Figure 25F:
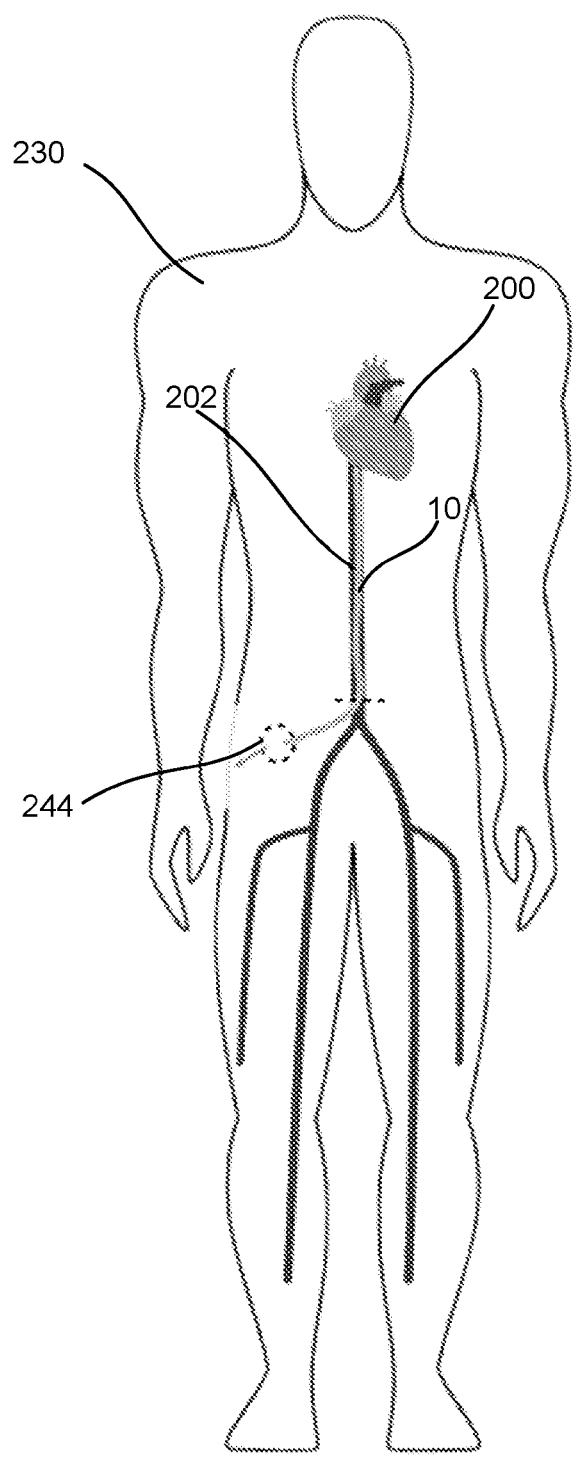
Figures 26A, 26B:
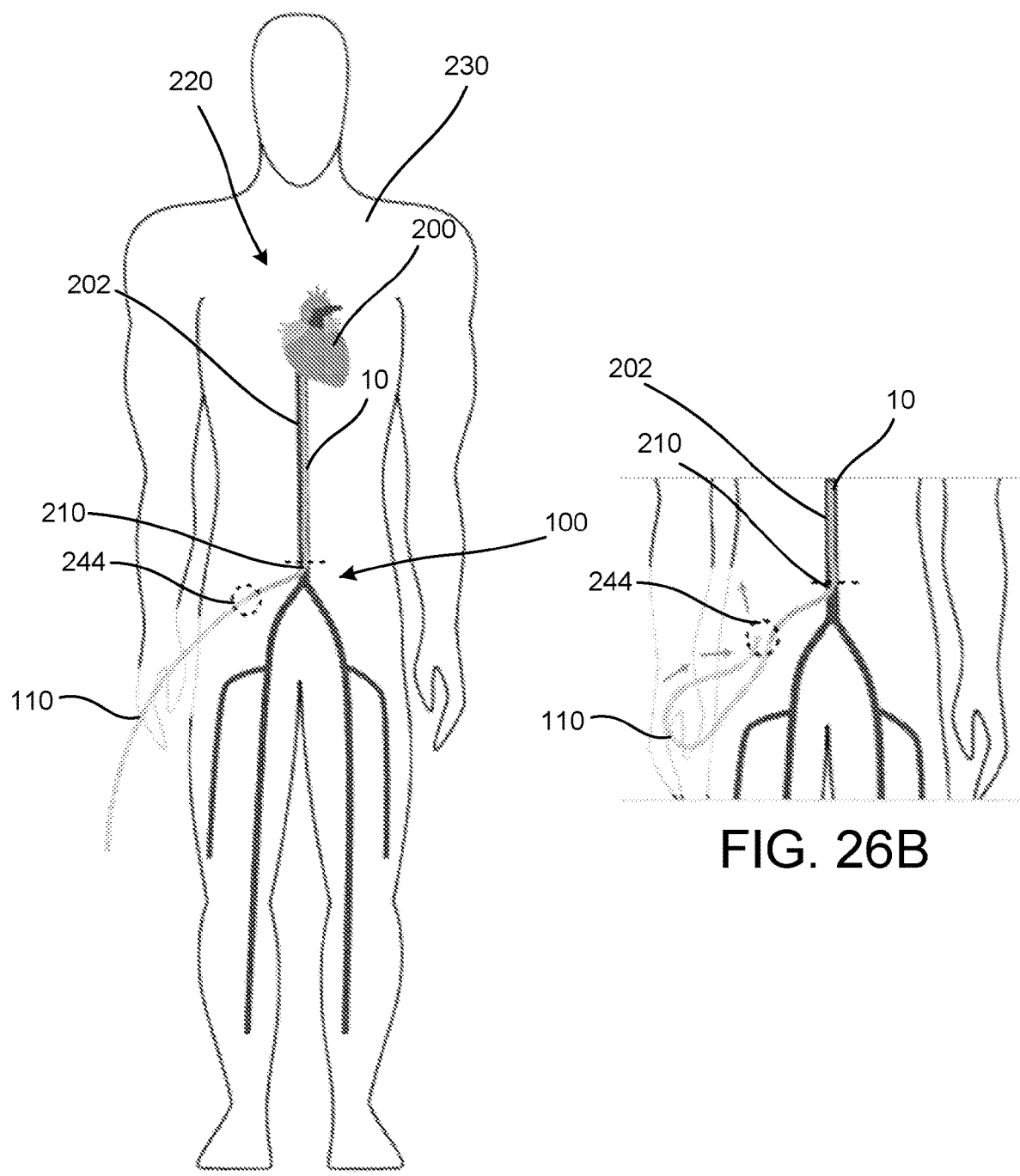
FIG. 26A is a schematic of the circulatory system of FIG. 22 illustrating an access site and insertion of a ventricular assist system of the present disclosure.
FIGS. 26B and 26C are schematics of the ventricular assist system of FIG. 26A and depict repositioning of a driveline of the present disclosure toward a treatment site from an access site.
Figure 26C:
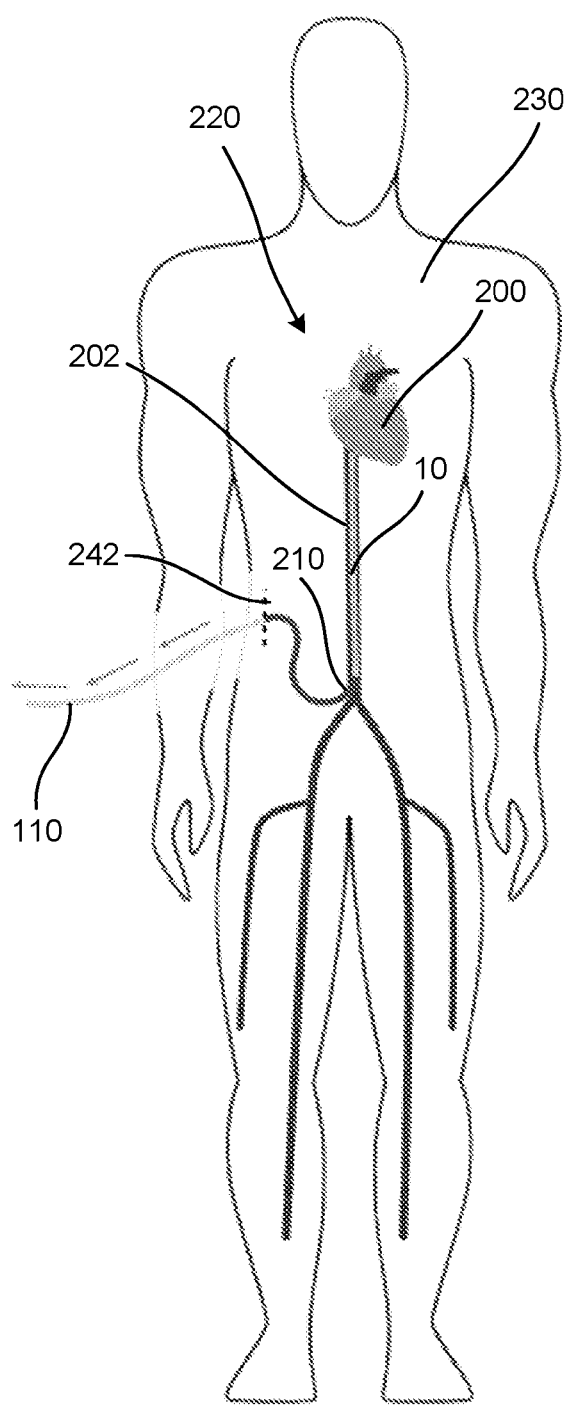
Figure 26D:
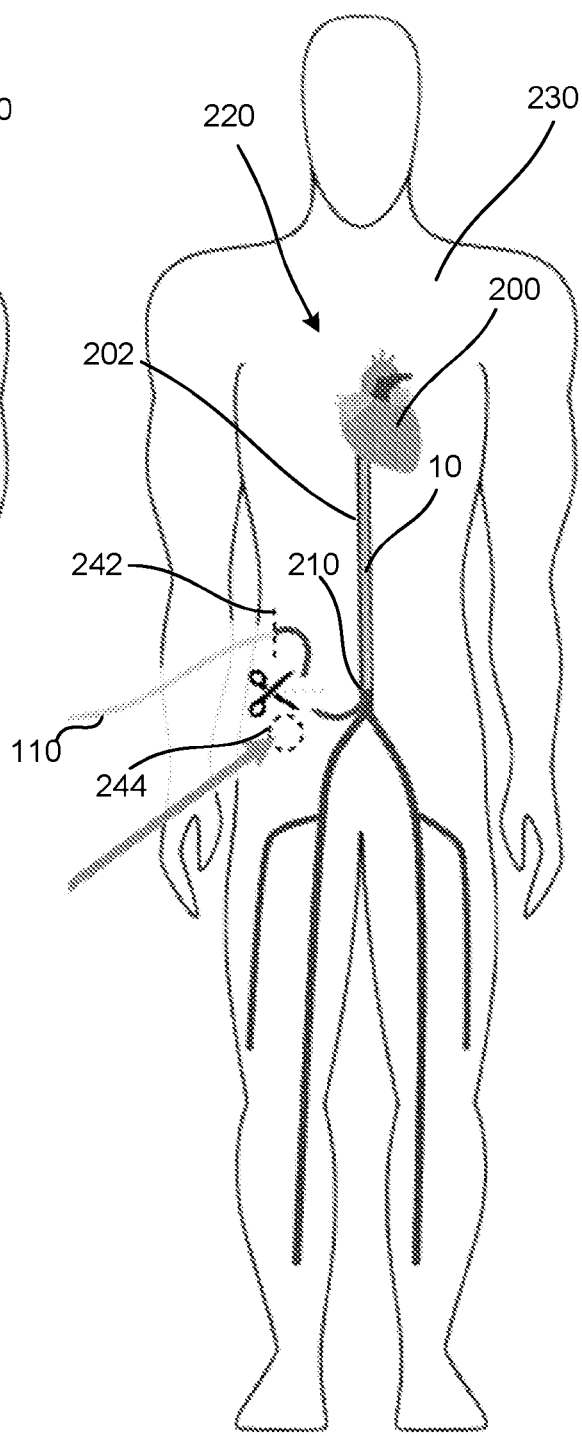
FIGS. 26D-26F are schematics of the ventricular assist system of FIGS. 26A-26C and depict removal of the ventricular assist system of the present disclosure.
Figure 26E:
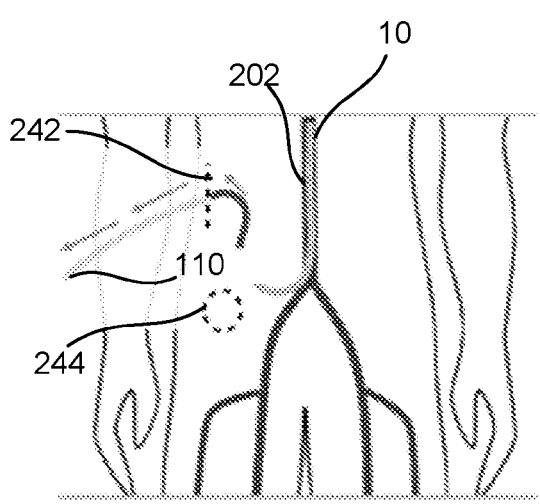
Figure 26F:
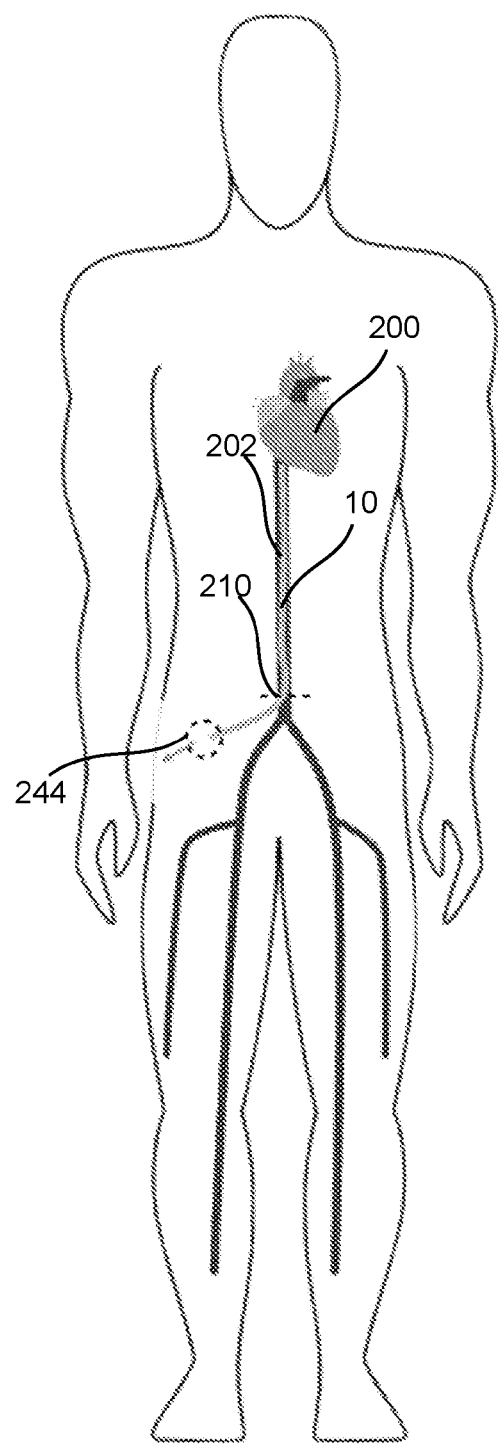
Figure 27:
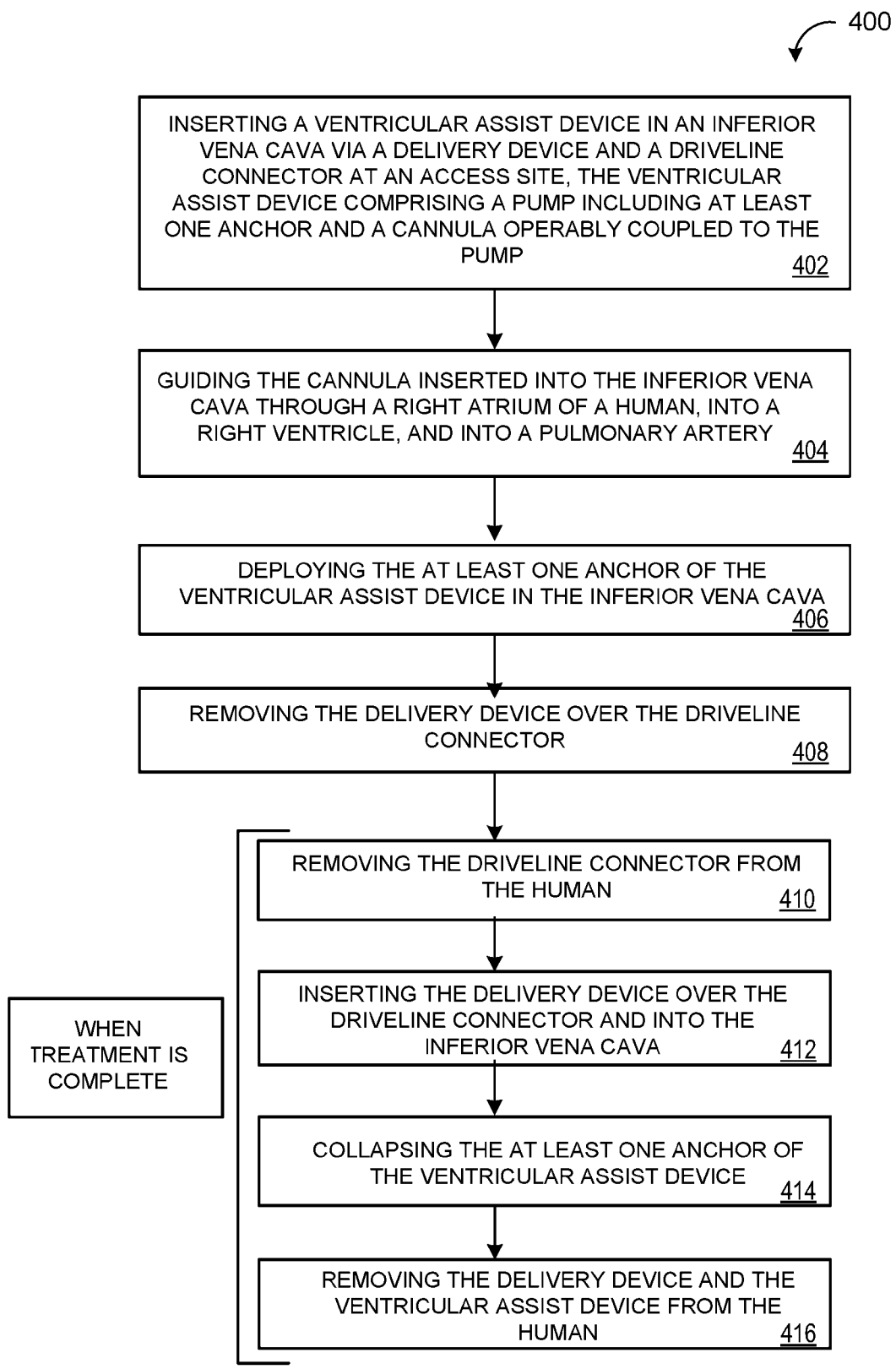
FIG. 27 is a flow diagram of a method of treatment using the ventricular assist system of the present disclosure.

Referring now to FIGS. 22-27, a method 400 of treatment of a cardiovascular impairment is described using the ventricular assist device 10 across the right ventricle 208 between the inferior vena cava 202 and the pulmonary artery 204 of a body 230, for example a human body. FIG. 22 illustrates a schematic figure of a human and a lower portion of a circulatory system 220. The circulatory system 220 includes femoral veins 222, which for purposes of this disclosure is discussed in relation to a single femoral vein 222, the inferior vena cava 202, the heart 200, and the pulmonary artery 204, among other arteries and veins. The inferior vena cava 202 extends between the femoral vein 222 and the heart 200 within an abdomen 232 of the body 230. The femoral vein 222 may be accessed via a thigh 234 of the human proximate a groin region 236.

The method 400 generally sets forth, at step 402, that the ventricular assist device 10 is inserted in the inferior vena cava 202 via the delivery device 120 and the driveline 110 at an access site 240, such as a femoral vein. For example, the cannula 12 of the ventricular assist device is inserted in the inferior vena cava 202. The cannula 12 of the ventricular assist device 10 is guided, at step 404, through the inferior vena cava 202 and the right atrium 206 and into the right ventricle 208. It is contemplated that the ventricular assist device 10, including the pump 24 and the cannula 12, may be rotated during implantation, which may optimize the anatomic positioning of the device 10. The cannula 12 is ultimately guided into the pulmonary artery 204. The pump anchor 26 is deployed, at step 406, in the inferior vena cava 202. Stated differently, at least one anchor 26a, 26b of the ventricular assist device is deployed in the inferior vena cava 202. The delivery device 120 is then removed, at step 408, over the driveline 110. When treatment is complete, the driveline 110 is at least partially removed, at step 410, from the body 230. The access site 240 is closed around the driveline 110, such that the driveline 110 is directed to a treatment site 242, such as at the abdomen, where the driveline 110 exits the body to interface with an external controller. Stated differently, the driveline 110 is subcutaneously tunneled from the access site 240 to the treatment site 242. It is contemplated that the driveline 110 remains external to the body 230 for the duration of treatment at the treatment site 242. The delivery device 120 is inserted, at step 412, over the partially removed driveline 110 and into the inferior vena cava 202. The pump anchor 26 of the ventricular assist device 10 is collapsed, at step 414, and the delivery device 120 and the ventricular assist device 10 are removed, at step 416, from the body 230. Each of these steps is described in more detail below.

With reference to FIGS. 22-24E, one implementation of the method 400 of treatment is illustrated. The ventricular assist system 100, which includes the ventricular assist device 10 and the delivery device 120, may be inserted into the body 230 at the access site 240. In this implementation, the access site 240 is proximate the femoral vein 222 along the thigh 234. The ventricular assist system 100 may be advanced through the vasculature toward the inferior vena cava 202 up to an inferior cavoatrial junction proximate the heart 200. As mentioned above, the cannula 12 is advanced through the right atrium 206 and right ventricle 208 and into the pulmonary artery 204. It is contemplated that the shape of the cannula 12 may be configured to minimize interference with the pulmonary valve. Additionally or alternatively, the tip anchor 26 illustrated in FIGS. 18A and 18B may be utilized to minimize interference with the pulmonary valve. It is further contemplated that the cannula 12 is disposed within the center of the pulmonary valve while valve leaflets will coapt around the cannula 12. The tip anchor 26 may assist in centering the cannula 12 within the valve to assist in improving coaptation of the valve leaflets against the cannula 12. For example, the cannula 12 may press against one of the valve leaflets if the cannula 12 is off-center. As discussed above, the pump anchor 26 is deployed and the delivery device 120 is removed over the driveline 110. It is contemplated that the driveline 110 may exit the body 230 at the access site 240. For example, the driveline 110 may be partially removed at the access site 240. It is contemplated that the access site 240 may provide access both to the femoral vein 222 as well as subcutaneous access within the body 230.

The driveline 110 may be fed into the access site 240 at an approximately 180-degree turn and directed subcutaneously from the access site 240 into the abdomen 232 in a superior direction. The driveline 110 may exit the abdomen 232 at a treatment site 242 where a treatment may be executed using the driveline 110 and the ventricular assist device 10. It is contemplated that the treatment site 242 may be, for example, at a subcostal or lower abdomen location. In this implementation, the access site 240 may be closed during treatment. Once treatment has concluded, the access site 240 may be reopened and the driveline 110 may be severed from the ventricular assist device 10. The severed driveline 110 may then be pulled retrograde back to the access site 240, and the delivery device 120 may be reinserted over the driveline 110 at the access site 240 to remove the ventricular assist device 10. The delivery device 120 deploys the sheath 102 to collapse the anchor 26, and the delivery device 120 and the ventricular assist device 10 may then be removed from the body 230 via the access site 240. It is also contemplated that a separate removal device, similar to the delivery device 120, may be utilized during removal of the device 10. In one example, the delivery device 120 may include a snare or other collapsing device that may be utilized to collapse the tip anchor 26 and covered by the sheath 102.

With reference now to FIGS. 22-23B and 25A-25F, an alternate implementation of the method 400 of treatment is illustrated. As discussed above, the ventricular assist system 100 may be inserted into the body 230 at the access site 240. In this implementation, the access site 240 is still proximate the femoral vein 222 along the thigh 234. The ventricular assist system 100 may be advanced through the inferior vena cava 202 up to an inferior cavoatrial junction proximate the heart 200. As mentioned above, the cannula 12 is advanced through the right atrium 206 and right ventricle 208 and into the pulmonary artery 204. As discussed above, the pump anchor 26 is deployed and the delivery device 120 is removed over the driveline 110. It is contemplated that the driveline 110 may exit the body 230 at the access site 240. For example, the driveline 110 may be partially removed at the access site 240. It is contemplated that the access site 240 may provide access both to the femoral vein 222 as well as subcutaneous access within the body 230.

Once partially removed, the driveline 110 may be bent extracorporeally and reinserted into the access site 240 toward a lower portion 210 of the inferior vena cava 202. The driveline 110 may be fed into the access site 240 at an approximately 180-degree turn and directed through the femoral vein 222 into the lower portion 210 of the inferior vena cava 202. An exit site 246 is defined at the lower portion 210 of the inferior vena cava 202, and an end of the driveline 110 may be guided subcutaneously toward the treatment site 242 in the lower abdomen 232 from the exit site 246 defined at the lower portion 210 of the inferior vena cava 202. The driveline 110 may be positioned subcutaneously from the inferior vena cava 202 toward the treatment site 242 at the abdomen 232. The treatment site 242 is defined, and the driveline 110 is removed at the treatment site 242. As mentioned above, the driveline 110 remains positioned at the treatment site 242 in the abdomen 232 for the duration of the treatment. Once treatment is complete, an abdominal access site 244 is opened, and the driveline 110 is severed. The severed driveline 110 may be removed via the abdominal access site 244, and the delivery device 120 may be inserted and positioned over the ventricular assist device 10 within the inferior vena cava 202. The delivery device 120 deploys the sheath 102 to collapse the anchor 26, and the delivery device 120 and the ventricular assist device 10 may then be removed from the body 230 via the abdominal access site 244.

With reference now to FIGS. 22 and 26A-26F, a third implementation of the method 400 of treatment is illustrated. The ventricular assist system 100 may be inserted into the body 230 at the access site 240. In this implementation, the access site 240 is positioned at the abdomen, such that the ventricular assist system 100 is inserted via the abdominal access site 244, and the abdominal access site 244 is proximate to the inferior vena cava 202. While discussed above as separate access points, it is contemplated that terminology of the access site 240 may be interchangeable with the abdominal access site 244 in the third implementation discussed herein.

The ventricular assist system 100 may be inserted through the lower portion 210 of the inferior vena cava 202 and advanced upward within the inferior vena cava 202 to an inferior cavoatrial junction proximate the heart 200. As mentioned above, the cannula 12 is advanced through the right atrium 206 and right ventricle 208 and into the pulmonary artery 204. As discussed above, the pump anchor 26 is deployed and the delivery device 120 is removed over the driveline 110. It is contemplated that the driveline 110 may exit the lower portion 210 of the inferior vena cava 202 and at least partially exit the abdominal access site 244.

The driveline 110 may be fed into the abdominal access site 244 at an approximately 180-degree turn and directed subcutaneously from the abdominal access site 244 into the abdomen 232 toward the treatment site 242. The treatment site 242 is defined in the abdomen 232 above the abdominal access site 244. Additionally or alternatively, the treatment site 242 may be defined below, adjacent, or otherwise proximal to the abdominal access site 244. As discussed above, the driveline 110 may exit the treatment site 242 during the duration of the treatment. In this implementation, the abdominal access site 244 may be closed during treatment. Once treatment has concluded, the abdominal access site 244 may be reopened and the driveline 110 may be severed from the ventricular assist device 10. The severed driveline 110 may then be removed from the treatment site 242, and the delivery device 120 may be reinserted at the abdominal access site 244 to remove the ventricular assist device 10 at the lower portion 210 of the inferior vena cava 202. The delivery device 120 deploys the sheath 102 to collapse the anchor 26, and the delivery device 120 and the ventricular assist device 10 may then be removed from the body 230 via the abdominal access site 244.

It is contemplated that the ventricular assist device 10 may cooperate with a pressure sensor during use. For example, a desired central venous pressure may fall within a range of approximately 0 mmHg to 10 mmHg and typical physiological limits are approximately 5 mmHg to 25 mmHg. The ventricular assist device 10 may function independent of the pressure sensor to maintain the pressure within the central venous pressure or may cooperate with the pressure sensor to maintain the central venous pressure within the desired range. The ventricular assist device 10 is also configured to meet hemodynamic requirements. In either configuration, the ventricular assist device 10 is configured to assist a failing ventricle of the heart. By way of example, not limitation, the ventricular assist device 10 may assist a failing right ventricle, such that the ventricular assist device 10 may be configured as a right ventricular assist device 10.

Each of these implementations provide various improvements to current treatment. For example, the first and second implementations provide a single vascular access point while avoiding direct contact with the inferior vena cava. In particular, the second implementation maximizes the ease of delivery of the ventricular assist device into the final functional position. The third implementation also provides a single vascular access site and minimizes the number of incisions of the body. In addition, the third implementation may provide for a shorter delivery device and a shorter driveline connection.

A number of implementations have been described. Nevertheless, it will be understood that various modifications may be made without departing from the spirit and scope of the disclosure. Accordingly, other implementations are within the scope of the following claims.

What is claimed is:

1. A ventricular assist device, comprising:
   a cannula defining a lumen and including a first end and a second end, the second end of the cannula including a tip that defines an opening for outflow of blood;
   a pump operably coupled to the first end of the cannula and having an inlet in fluid communication with the opening;
   a pump anchor operably coupled to the pump, the pump anchor having a retracted position and a deployed position; and
   a tip anchor operably coupled to the second end of the cannula proximate the tip;
   wherein the pump anchor and the tip anchor each include an attachment portion and a plurality of extensions extending from the attachment portion, and wherein the pump anchor and the tip anchor are coupled to the pump and the second end of the cannula, respectively, at the respective attachment portions;
   wherein the plurality of extensions of the pump anchor define an interconnected net disposed around the pump such that the inlet of the pump in use intakes the blood in circulation upstream ahead of the blood passing through apertures of the interconnected net; and
   wherein the pump anchor includes a plurality of eyelets and a wire disposed through the plurality of eyelets and configured to be drawn to draw the plurality of eyelets closer to one another.

2. The ventricular assist device of claim 1, wherein the cannula includes a semi-rigid sigmoidal body defined between the first end and the second end.

3. The ventricular assist device of claim 1, wherein the tip has a lower arcuate portion and an upper narrow portion that collectively define the opening.

4. The ventricular assist device of claim 1, wherein the pump anchor includes a first pump anchor coupled to the pump and a second pump anchor coupled to the pump, and wherein each of the first and second pump anchors include a plurality of extensions.

5. The ventricular assist device of claim 4, wherein the plurality of extensions of the first pump anchor extend toward the cannula and the plurality of extensions of the second pump anchor extend away from the cannula.

6. The ventricular assist device of claim 1, wherein the plurality of eyelets are proximate one another in the retracted position of the pump anchor.

7. The ventricular assist device of claim 1, wherein the pump anchor includes the plurality of eyelets at an opposing end from the attachment portion of the pump anchor.

* * * * *